(12) United States Patent
Goelman et al.

(10) Patent No.: US 7,982,462 B2
(45) Date of Patent: Jul. 19, 2011

(54) SYSTEM, METHOD AND COMPUTER ACCESSIBLE MEDIUM FOR MAGNETIC RESONANCE SPECTROSCOPIC IMAGING

(75) Inventors: Gadi Goelman, Rosh Haain (IL); Oded Gonen, Leonardo, NJ (US)

(73) Assignee: New York University, New York, NY (US)

( * ) Notice: Subject to any disclaimer, the term of this patent is extended or adjusted under 35 U.S.C. 154(b) by 53 days.

(21) Appl. No.: 12/135,837

(22) Filed: Jun. 9, 2008

(65) Prior Publication Data

US 2009/0085564 A1 Apr. 2, 2009

Related U.S. Application Data

(60) Provisional application No. 60/942,694, filed on Jun. 8, 2007.

(51) Int. Cl.
*G01V 3/00* (2006.01)
(52) U.S. Cl. ........................................ 324/309
(58) Field of Classification Search .......... 324/300–322; 600/410–435; 333/219–235; 702/1–32, 702/189–199
See application file for complete search history.

(56) References Cited

U.S. PATENT DOCUMENTS

| | | | | |
|---|---|---|---|---|
| 3,968,424 A * | 7/1976 | Ernst | | 324/310 |
| 4,698,593 A * | 10/1987 | Crooks | | 324/309 |
| 4,868,501 A * | 9/1989 | Conolly | | 324/309 |
| 5,285,156 A * | 2/1994 | Bodenhausen et al. | | 324/307 |
| 5,285,159 A * | 2/1994 | Bodenhausen et al. | | 324/314 |
| 5,353,795 A * | 10/1994 | Souza et al. | | 600/423 |
| 5,548,216 A * | 8/1996 | Dumoulin et al. | | 324/309 |
| 5,581,181 A * | 12/1996 | Fuderer | | 324/309 |
| 5,615,677 A * | 4/1997 | Pelc et al. | | 600/410 |
| 5,903,149 A * | 5/1999 | Gonen et al. | | 324/307 |
| 5,952,827 A * | 9/1999 | Feinberg | | 324/309 |
| 6,144,873 A * | 11/2000 | Madore et al. | | 600/410 |
| 6,320,378 B1 * | 11/2001 | Maier et al. | | 324/307 |
| 6,377,042 B1 * | 4/2002 | Menger et al. | | 324/303 |
| 6,456,072 B1 * | 9/2002 | Webb et al. | | 324/308 |
| 6,477,398 B1 * | 11/2002 | Mills | | 600/409 |
| 7,382,129 B2 * | 6/2008 | Mills | | 324/318 |

(Continued)

OTHER PUBLICATIONS

Goelman et al.; Optimizing the efficiency of high-field multivoxel spectroscopic imaging by multiplexing in space and time; Magnetic Resonance in Medicine 56; 2006, pp. 34-40.*

(Continued)

*Primary Examiner* — Dixomara Vargas
(74) *Attorney, Agent, or Firm* — Dorsey & Whitney LLP

(57) ABSTRACT

An exemplary embodiment of system, method, and computer accessible medium for magnetic resonance spectroscopic imaging for improving signal-to-noise ratio per unit time and optimizing duty cycle in MRSI and/or for reducing chemical-shift artifacts can be provided. In one exemplary embodiment, an excitation pulse can be forwarded to the target and acquiring a signal from the target by multiplexing in time and space. The multiplexing procedure in time can involve (i) a segmentation of a field of view of the at least one portion of the target into a predetermined number of slabs that are acquired sequentially during each repetition time, and/or (ii) an acquisition of multiple voxels. Data can be generated based on the acquired signal. According to another exemplary embodiment, an excitation pulse can be provided to the target, and a signal can be acquired from the target. The excitation pulse can be a series of cascaded Hadamard pulse components. Data can be generated based on the acquired signal.

37 Claims, 11 Drawing Sheets

U.S. PATENT DOCUMENTS 7,514,927 B2 *   4/2009   Herzka et al. ............... 324/318

OTHER PUBLICATIONS

Adalsteinsson, Elfar et al., "Three-Dimensional Spectroscopic Imaging with Time-Varying Gradients", *Magn Reson Med* 33(4) 1995, 461-466.

Adalsteinsson, Elfar et al., "Volumetric Spectroscopic Imaging with Spiral-Based k-Space Trajectories", *Magn Reson Med* 39(6) 1998, 889-898.

Brown, T. R. et al., "NMR Chemical Shift Imaging in Three Dimensions", *Proc Nat Acad USA* 79 Jun. 1982, pp. 3523-3526.

Brown, Truman R., "Practical Applications of Chemical Shift Imaging", *NMR in Biomedicine*, vol. 5 1992, 238-243.

Chu, Archie et al., "Proton Echo-Planar Spectroscopic Imaging With Highly Effective Outer Volume Suppression Using Combined Presaturation and Spatially Selective Echo Dephasing", *Magnetic Resonance in Medicine* 49 2003, 817-821.

Dreher, Wolfgang et al., "A New Method for Fast Proton Spectroscopic Imaging: Spectroscopic GRASE", *Magnetic Resonance in Medicine* 44 2000, 668-672.

Dreher, Wolfgang et al., "Double-Echo Multislice Proton Spectroscopic Imaging Using Hadamard Slice Encoding", *MRM* 31 1994, 596-600.

Dreher, Wolfgang et al., "Fast Proton Spectroscopic Imaging With High Signal-to-Noise Ratio: Spectroscopic RARE", *Magnetic Resonance in Medicine* 47 2002, 523-528.

Duyn, Jeff H. et al., "Fast Proton Spectroscopic Imaging of Human Brain Using Multiple Spin-Echoes", *MRM* 30 1993, 409-414.

Duyn, Jeffrey H. et al., "Multisection Proton MR Spectroscopic Imaging of the Brain", *Radiology* vol. 188, No. 1 1993, 277-282.

Ebel, Andreas et al., "A Fast Variant of 1H Spectroscopic U-FLARE Imaging Using Adjusted Chemical Shift Phase Encoding", *Journal of Magnetic Resonance* 142 2000, 241-253.

Ernst, Richard R. et al., "Principles of Nuclear Magnetic Resonance in One and Two Dimensions", *The International Series of Monographs on Chemistry*, Oxford: Clarendon Press 1987, 152.

Goelman, Gadi, "Fast 3D T2-weighted MRI with Hadamard Encoding in the Slice Select Direction", *Magnetic Resonance Imaging* 18 2000, 939-945.

Goelman, Gadi et al., "Hadamard Spectroscopic Imaging Techniques as Applied to Study Human Calf Muscles", *Magn Reson Med* 25 1992, 349-354.

Goelman, Gadi et al., "Reducing Voxel Bleed in Hadamard-Encoded MRI and MRS", *Magn Reson Med* 55(6) 2006, 1460-1465.

Goelman, Gadi et al., "Transverse Hadamard Spectroscopic Imaging", *J Magn Reson* 89 1990, 437-454.

Gonen, Oded et al., "3D Localized in Vivo 1H Spectroscopy of Human Brain by Using a Hybrid of 1D-Hadamard with 2D-Chemical Shift Imaging", *MRM* 37 1997, 644-650.

Gonen, Oded et al., "Hybrid Three Dimensional (1D-Hadamard, 2D-Chemical Shift Imaging) Phosphorus Localized Spectroscopy of Phantom and Human Brain", *MRM* 33 1995, 300-308.

Gonen, Oded et al., "Multivoxel 3D Proton Spectroscopy in the Brain at 1.5 Versus 3.0 T: Signal-to-Noise Ratio and Resolution Comparison", *AJNR Am J Neuroradiol* 22 Oct. 2001, 1727-1731.

Hoult, D. I., "The NMR Receiver: A Description and Analysis of Design", *Progress in NMR Spectroscopy*, vol. 12 1978, 41-77.

Hu, J. et al., "A Fast, Reliable, Automatic Shimming Procedure Using 1H Chemical-Shift-Imaging Spectroscopy", *J Magn Reson B* 108(3) 1995, 213-219.

Johnson, Glyn et al., "2D Multislice and 3D MRI Sequences Are Often Equally Sensitive", *Magnetic Resonance in Medicine* 41 1999, 824-828.

Kim, Dae-Shik et al., "High-field magnetic Resonance Techniques for Brain Research", *Current Opinion in Neurobiology* 2003, 612-619.

Macovski, Albert, "Noise in MRI", *MRM* 36 1996, 494-497.

Marion, Dominique et al., "Improved Solvent Suppression in One- and Two-Dimensional NMR Spectra by Convolution of Time-Domain Data", *Journal of Magnetic Resonance* 84 1989, 425-430.

Maudsley, A. A. et al., "Spatially Resolved High Resolution Spectroscopy by "Four-Dimensional" NMR", *Journal of Magnetic Resonance* 51 1983, 147-152.

Oded, Gonen et al., "3D Multivoxel Proton Spectroscopy of Human Brain Using a Hybridge of 8th-Order Hadamard Encoding With 2D Chemical Shift Imaging", *MRM* 39 1998, 34-40.

Posse, Stefan et al., "Short Eco Time Proton MR Spectroscopic Imaging", *Journal of Computer Assisted Tomography* 17(1): 1993, 1-14.

Posse, Stefan et al., "Three-dimenstional Echo-planar MR Spectroscopic Imaging at Short Echo Times in the Human Brain", *Radiology* 192 1994, 733-738.

Soher, Brian J. et al., "Automated Spectral Analysis III: Application to in Vivo Proton MR Spectroscopy and Spectroscopic Imaging", *MRM* 40 1998, 822-831.

* cited by examiner

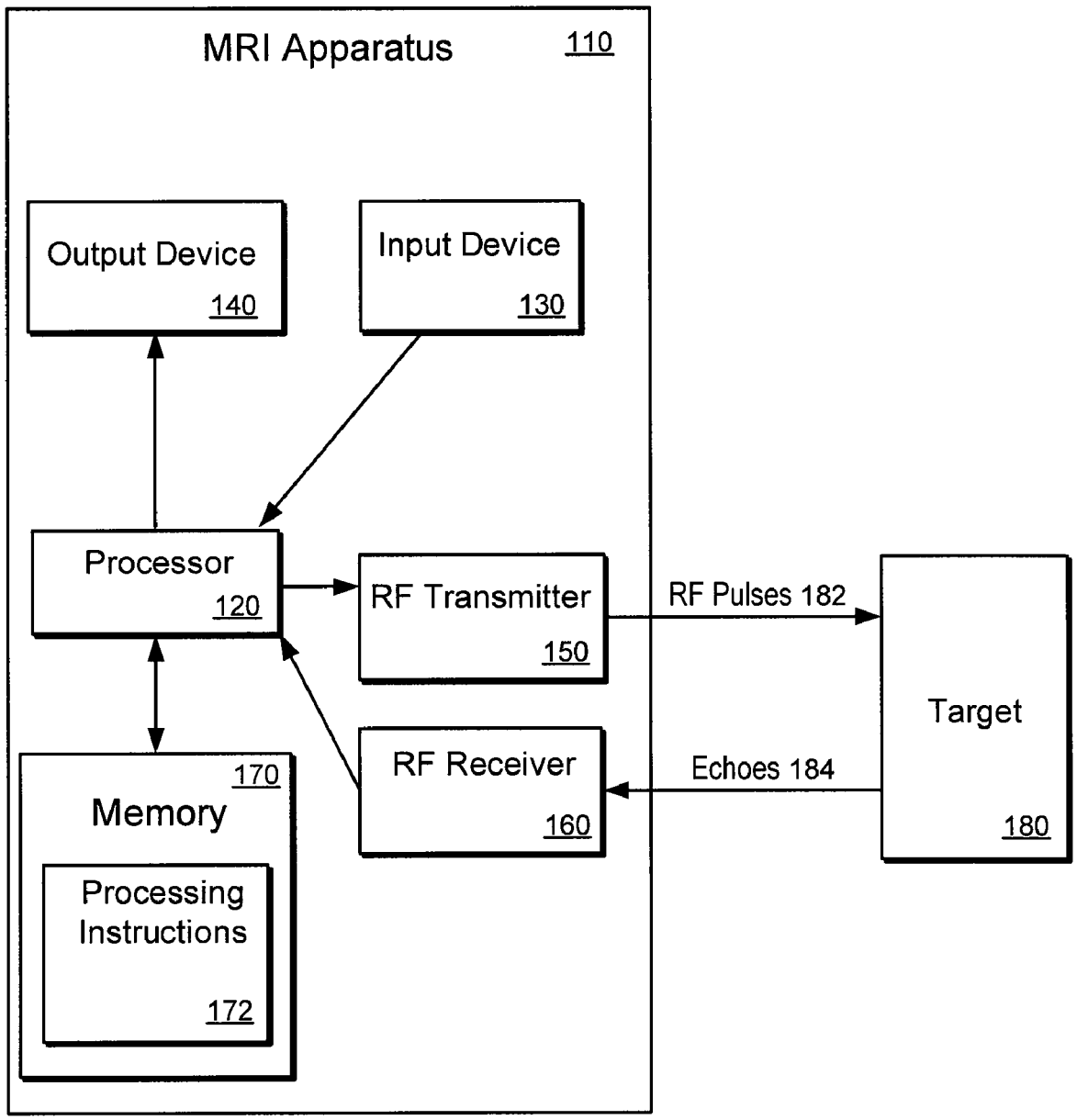
F I G. 1a

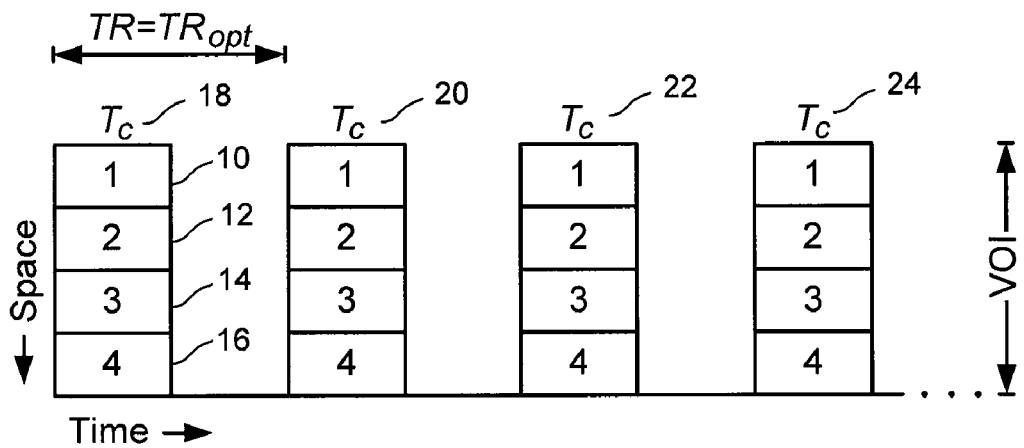
F I G. 2a
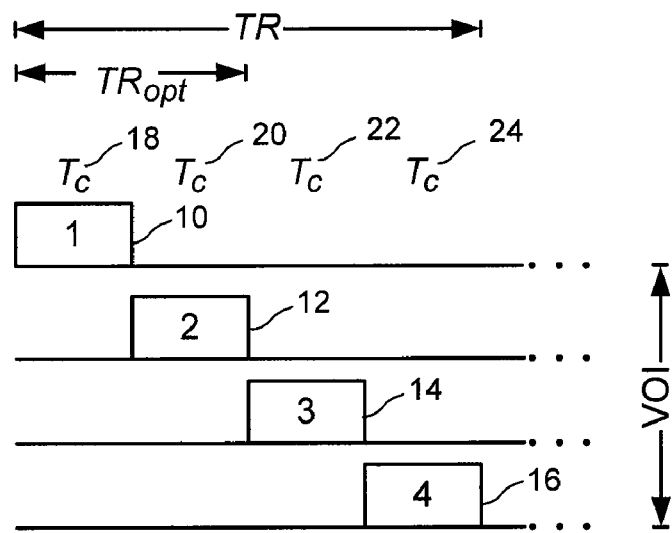
F I G. 2b
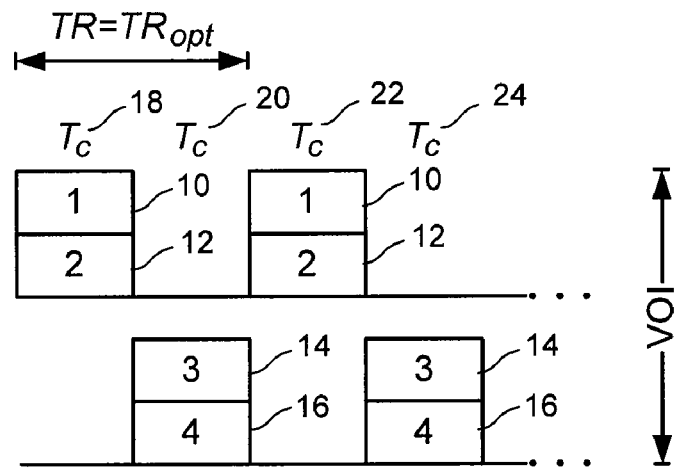
F I G. 2c

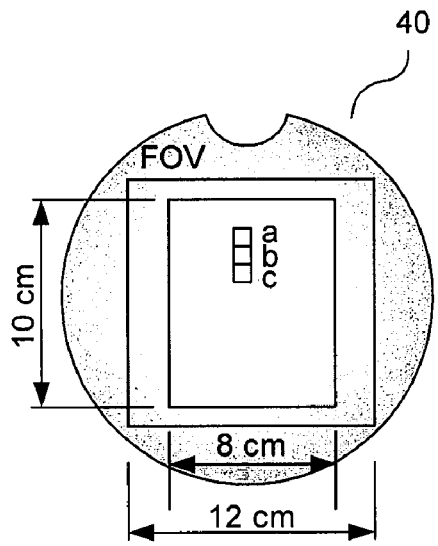
FIG. 4d
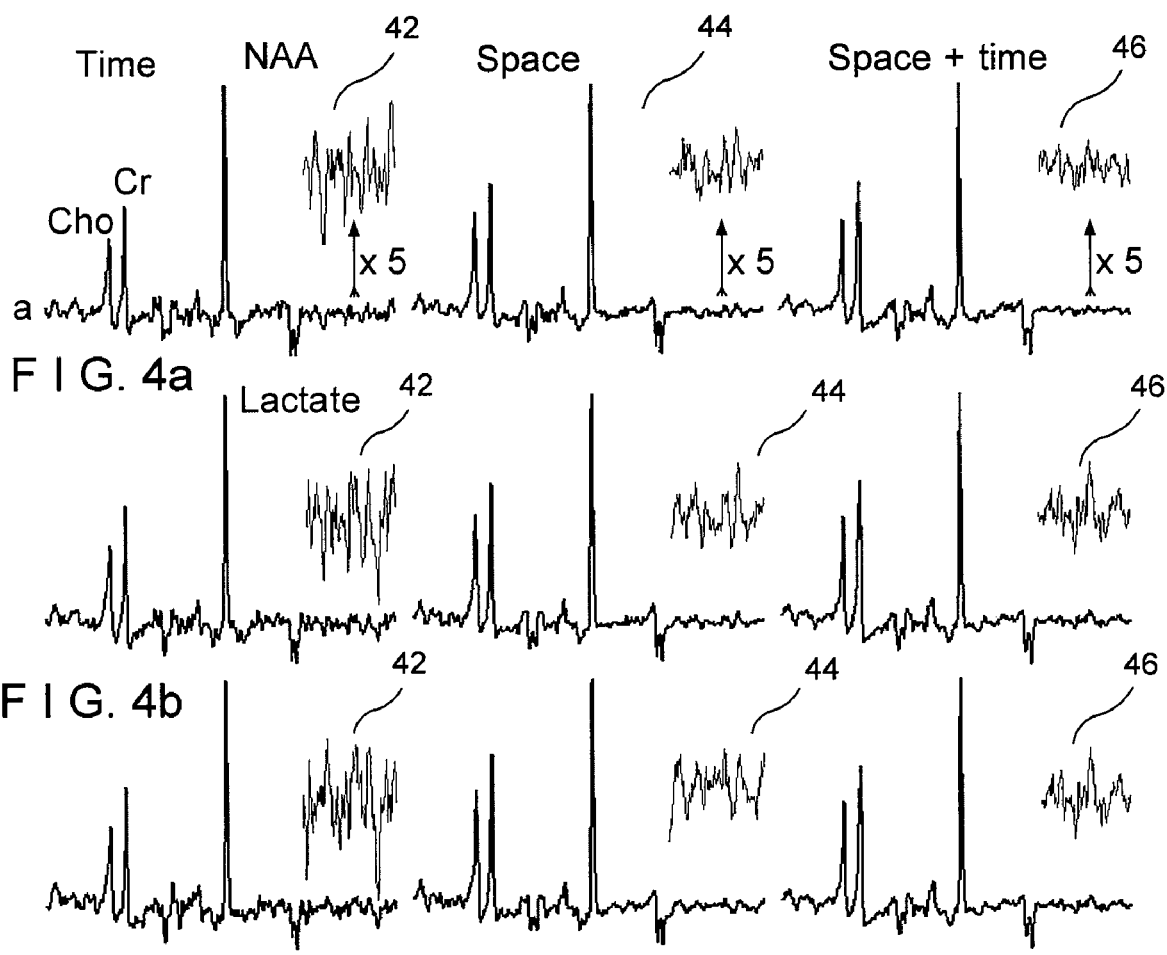
FIG. 4a
FIG. 4b
FIG. 4c

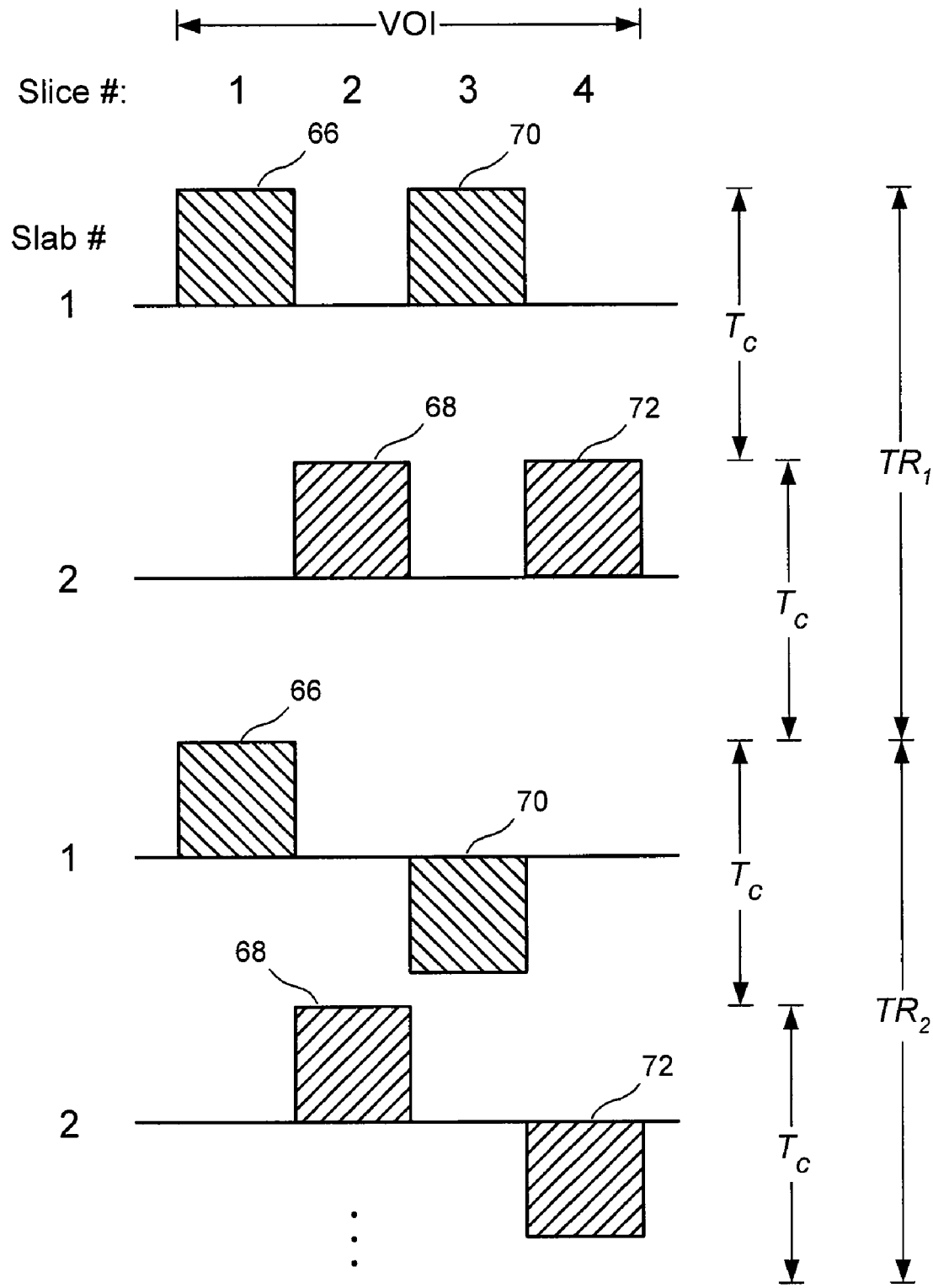
F I G. 6

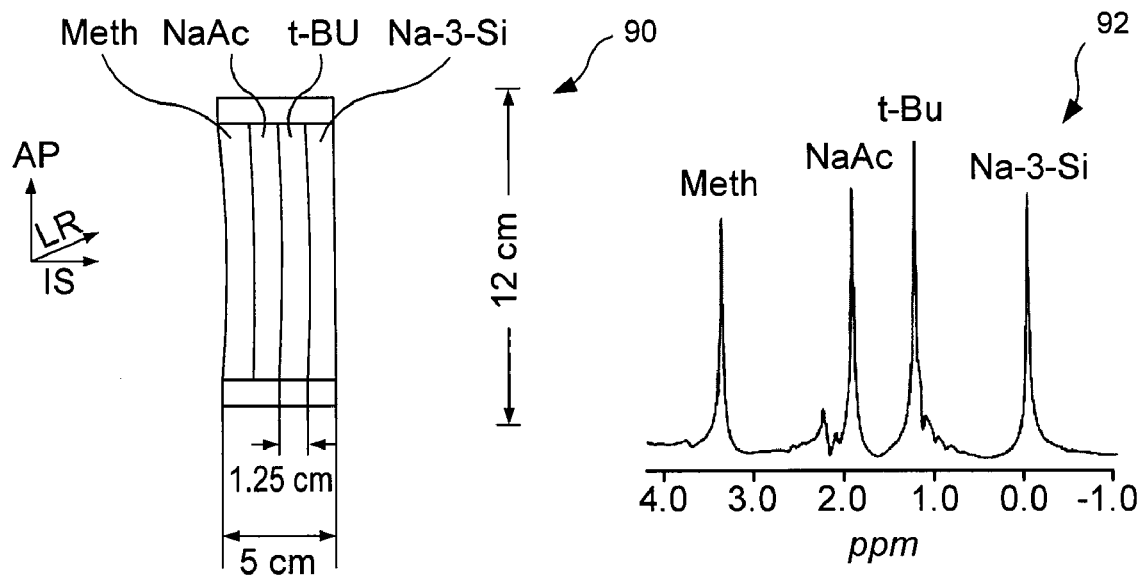
F I G. 8a
F I G. 8b
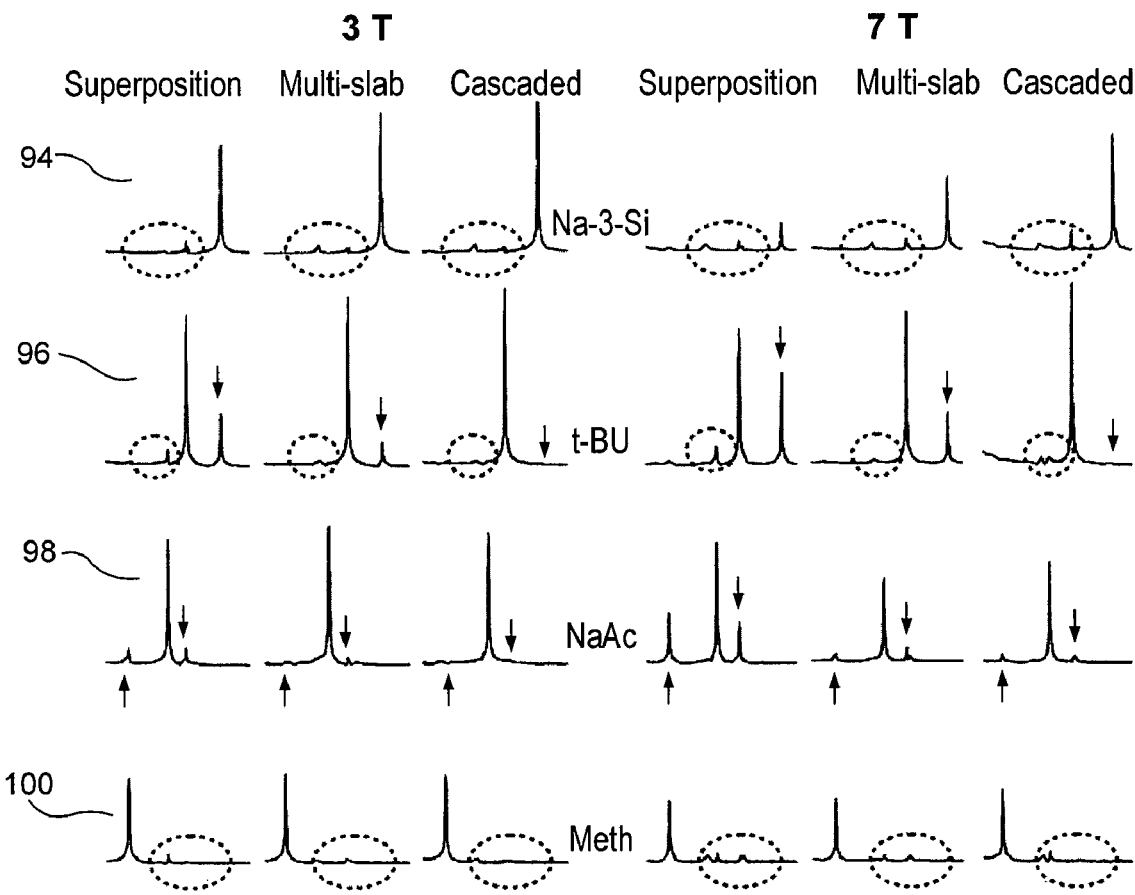
F I G. 8c

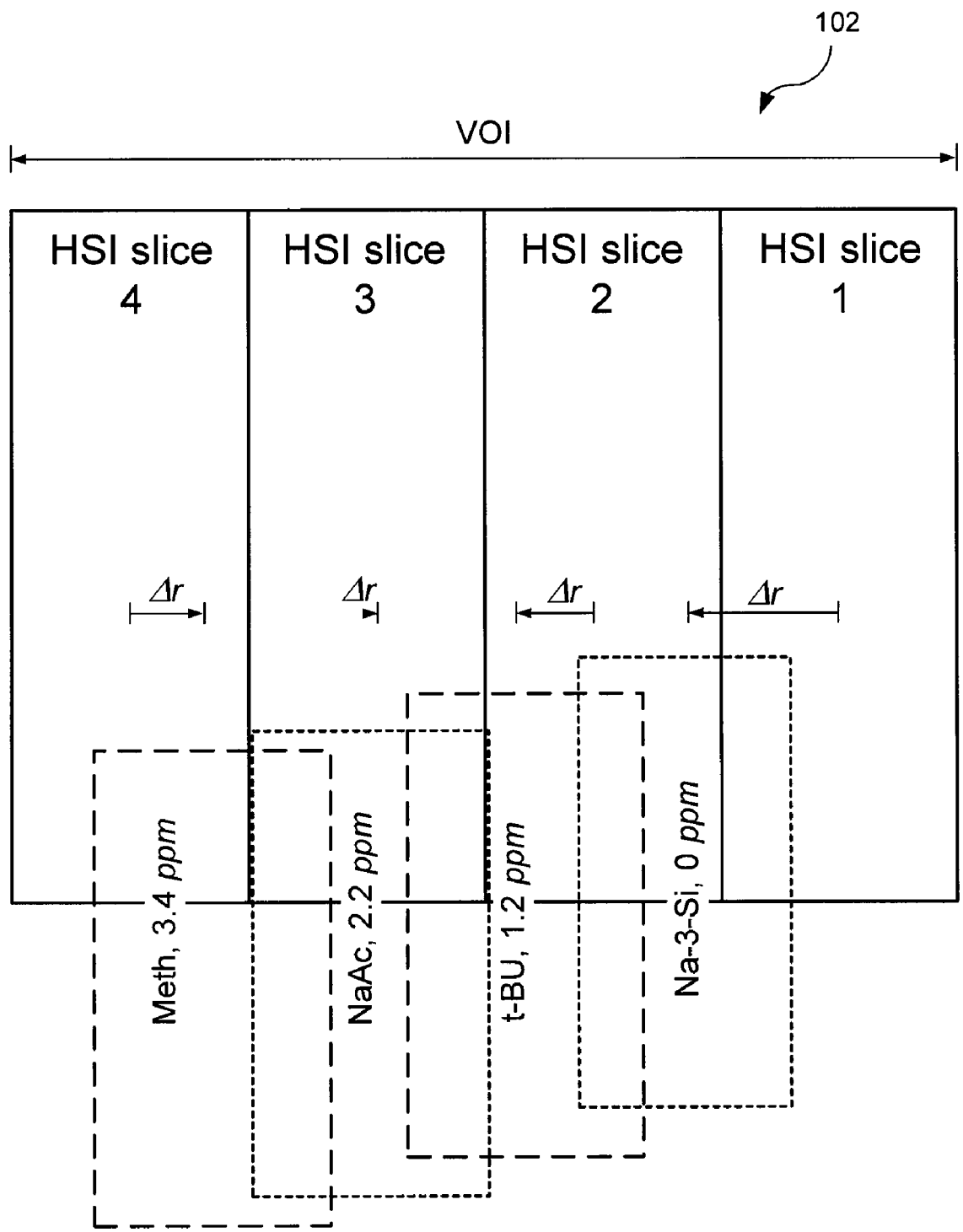
F I G. 9

SYSTEM, METHOD AND COMPUTER ACCESSIBLE MEDIUM FOR MAGNETIC RESONANCE SPECTROSCOPIC IMAGING

CROSS-REFERENCE TO RELATED APPLICATIONS

This application claims the benefit of priority from U.S. Patent Application Ser. No. 60/942,694, filed Jun. 8, 2007, the entire disclosure of which is incorporated herein by reference.

STATEMENT REGARDING FEDERALLY-SPONSORED RESEARCH

The invention was developed with the U.S. Government support from the National Institute of Health under NIH Grant Nos. EB01015, NS050520 and NS39135. Thus, the U.S. Government may have certain rights in the invention.

FIELD OF THE INVENTION

The present invention relates generally to a method of magnetic resonance spectroscopic imaging and, more particularly, to a method of magnetic resonance spectroscopic imaging that for improves signal-to-noise ratio per unit time and optimizes duty cycle and/or for reduces chemical-shift artifacts at high magnetic fields.

BACKGROUND INFORMATION

Magnetic resonance spectroscopy ("MRS") provides in vivo information regarding the concentration of specific metabolites (e.g., shown in parts per million, or ppm) in localized regions of the brain. Various challenges exist in MRS technology. Among these are SNR issues, relating to the very low concentration of metabolites as compared to water, and chemical shift displacements at higher magnetic fields when spatially-selective excitation is used.

In proton magnetic resonance imaging ("MRI") ($^1$H MRI), the image signal mainly relies on the proton of water, abundant in vivo. This hydrogen proton signal is the basis of MRI collection and without it, no MRI data can likely be collected. In contrast, in MRS data collection, special water suppression methods are used to suppress the proton signal from water to visualize the proton signals from the low-concentration metabolites, which range from 1 mM to 10 mM.

In image processing, the signal-to-noise ratio ("SNR") of an image is usually defined as the ratio of the mean pixel value to the standard deviation of the pixel values. MRS can yield an inferior signal-to-noise ratio per unit time as compared with MRI because concentrations of brain metabolites may be of orders of magnitude lower as compared with tissue water. Several techniques have been developed to compensate for the low SNR of MRS.

To improve SNR, MRS voxels can be typically more than one thousand times larger than those of MRI, e.g., on the order of cubic centimeters rather than cubic millimeters, and acquisition times may be on the order of 100-1000 times longer, e.g., many minutes as compared with a few seconds. Substantial technical and methodological efforts have been dedicated to improve the SNR and reduce the acquisition time of MRS, especially with respect to proton ($^1$H) variants, which may be prevalent because they can use the same hardware.

Another technique for improving SNR, for example, comprises multiplexing in space. Multiplexing in space may comprise increasing the spatial coverage from single- to simultaneous multi-voxel acquisition. Such MRS imaging (MRSI) can provide more spatial information at a similar SNR as determined by the voxel size and acquisition time. See, for example, *NMR Chemical Shift Imaging in Three Dimensions*, Brown T R et al., Proc Nat Acad USA 1982; 79:3523-3526; *Spatially Resolved High Resolution Spectroscopy by "Four Dimensional" NMR*, Maudsley et al., J Magn Reson 1983; 51:147-152; *Short Echo Time Proton MR Spectroscopic Imaging*, Posse et al., J Comput Assist Tomogr 1993; 17(1): 1-14; *Noise in MRI*, Macovski A., Magn Reson Med 1996; 36(3):494-497, all incorporated herein by reference in their entireties. To reduce SNR loss from incomplete longitudinal relaxation, $T_1$, the TR can be extended beyond the actual acquisition-cycle, $T_C$, the time needed to prepare and acquire one transient, which may be determined primarily by the desired spectral resolution. Because such system "recovers" during the period (TR–$T_C$), its duty cycle ("DC") can be inherently suboptimal, e.g., <100%.

A further technique which may be applied to proton MR spectroscopic imaging ($^1$H-MRSI) comprises multiplexing in time. This technique can maximize the amount of information obtained per unit time by increasing the DC, as described by Duyn et al. in *Fast Proton Spectroscopic Imaging of Human Brain Using Multiple Spin-Echos*, Magn Reson Med 1993; 30(4):409-414, incorporated herein by reference in its entirety. Multiplexing in time may comprise acquiring several $T_C$-s for every TR, where each can be obtained from a different slice. Reference is made to *Multisection Proton MR Spectroscopic Imaging of the Brain*, Duyn et al., Radiology 1993; 30(4):409-414, incorporated herein by reference in its entirety. This technique can, in some situations, lead to a suboptimal SNR. For example, TR may be longer than the optimal, $TR_{opt}$, in order to satisfy spatial coverage and spectral resolution requirements, which can lead to a suboptimal SNR.

A technique for 3D-multislab MRI comprises multiplexing in both space and time and is described by Goelman in *Fast 3D T(2)-weighted MRI with Hadamard Encoding in the Slice Select Direction*, Magn Reson Imaging 2000; 18(8);939-945, incorporated herein by reference in its entirety.

Another challenge arising in SNR technology is chemical shift displacements ("CSD"). Selective radio frequency (RF) pulses applied under a gradient can excite spins in different spatial bands during $^1$H-MRSI. Such bands can be displaced relative to each other by a distance, $\Delta r$, in the gradient direction, r (e.g., an X, Y or Z direction), as discussed by Kim et al. in *High-field Magnetic Resonance Techniques for Brain Research*, Curr Opin Neurobiol 2003; 13(5):612-619, incorporated herein by reference in its entirety. The displacement, which can be referred to as a "chemical shift artifact," can depend on a resonance frequency difference of the spins, $\Delta \omega_i$, and thus, e.g., on the magnetic field, $B_0$.

Higher values of $B_0$, therefore, can present conflicting requirements with respect to $^1$H-MRSI analyses. For example, providing a stronger $G_r$ to maintain or reduce relative magnitude and direction of the CSD, $\Delta r$, for better localization accuracy can require a higher RF pulse bandwidth ("BW") to retain a given field-of-view ("FOV") and flip-angle. However, higher power which may be needed to produce the same RF field ($B_1$) (e.g., the power required at 7 T can be twice that required at 4 T), may preclude any meaningful gradient increases. Consequently, while $\Delta r$ can increase with $B_0$, it may not be possible to significantly boost $G_r$ to mitigate this effect, and often it can be made even weaker to accommodate lesser $B_1$ values, which may exacerbate the displacement.

Thus, there may be a need for improved MRS techniques, and e.g., $^1$H-MRSI techniques, which may overcome some of the difficulties and limitations described herein above.

These and other objects, features and advantages of the present invention will become apparent upon reading the following detailed description of embodiments of the invention, when taken in conjunction with the appended claims.

SUMMARY OF THE EXEMPLARY EMBODIMENTS

To address at least some of the deficiencies described above, exemplary embodiments of systems and methods for MRSI for improving signal-to-noise ratio per unit time and optimizing duty cycle in magnetic resonance spectroscopic imaging and/or for reducing chemical-shift artifacts at high magnetic fields can be provided.

In exemplary embodiments of the present invention, optimal SNR and acquisition efficiency may be achieved simultaneously by multiplexing several slabs of several slices in space and time in MRSI. This exemplary embodiment can utilize the advantages of obtaining information from a maximum number of voxels, each at an optimal signal-to-noise ratio ("SNR") per unit time, in magnetic resonance spectroscopic imaging ("MRSI"). Conventional maximum acquisition duty-cycle may be obtained by multiplexing in time several single-slices for each repetition time ("TR"), while optimal SNR can be achieved by encoding the entire volume-of-interest ("VOI") for each TR. For a particular exam length, the techniques described herein can provide twice as many voxels at, for example, 3 T, each voxel having the same SNR and size, as compared with conventional 3-dimensional chemical shift imaging techniques. This exemplary gain can increase for more extensive spatial coverage or higher fields.

In a further exemplary embodiment of the present invention chemical-shift artifacts in MRSI at high magnetic fields are reduced by segmenting a VOI into several slabs, which can facilitate the use of a proportionally stronger slice-select gradient. In another exemplary embodiment for reducing chemical shift artifacts, sequentially cascading, rather than superimposing, components of Hadamard selective pulses may be used to provide an improved point-spread-function and to localize the few slices within each slab. This exemplary technique can reduce the peak value of $B_1$ to that of a single slice.

Thus, in yet a further exemplary embodiment of reducing chemical shift artifacts, the techniques of segmenting a VOI into several slabs and sequentially cascading components of Hadamard selective pulses may be combined. Combining these exemplary techniques can facilitate an increase in the selective gradient by a factor of about 4 to 8 per given $B_1$, e.g., to 12 or 18 mT/m for 4 or 2 cm VOI values. This exemplary approach may reduce the CSD to less than about 0.05 cm/ppm at 7 T or less than half that at 3 T.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 1a is a diagram of an exemplary embodiment of a system according to the present invention;

FIG. 2a is a schematic illustration of multiplexing in space in accordance with exemplary embodiments of the present invention;

FIG. 2b illustrates a schematic representation of multiplexing in time in accordance with the exemplary embodiment of the present invention;

FIG. 2c illustrates a schematic representation of multiplexing in space and time, in accordance with one exemplary embodiment of the present invention;

FIG. 4a illustrates $^1$H Spectra for three sample voxels from a first experiment in accordance with the exemplary embodiment of the present invention;

FIG. 4b illustrates $^1$H Spectra for three sample voxels from a second experiment in accordance with a particular exemplary embodiment of the present invention;

FIG. 4c illustrates $^1$H Spectra for three sample voxels from a third experiment in accordance with a certain exemplary embodiment of the present invention;

FIG. 4d illustrates an axial T1-weighted MRI image obtained in accordance with an exemplary embodiment of the present invention;

FIG. 6 illustrates multiplexing several slabs, one per acquisition cycle ($T_c$) within each repetition time (TR), in accordance with an exemplary embodiment of the present invention;

FIG. 8a illustrates a sagittal image of a phantom in accordance with the exemplary embodiment of the present invention;

FIG. 8b illustrates an absolute 3 T spectrum in accordance with the exemplary embodiment of the present invention;

FIG. 8c illustrates spectra from four voxel columns along the IS direction encoded with superposition, multi-slab, and cascaded multi-slab HIS in accordance with the exemplary embodiment of the present invention; and FIG. 9 illustrates a schematic representation of the location of four HIS RF excitation bands in accordance with a certain exemplary embodiment of the present invention.

Throughout the figures, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments.

DETAILED DESCRIPTION OF PREFERRED EMBODIMENTS

In accordance with certain exemplary embodiments of the present invention, systems, methods, and computer-accessible medium for improving signal-to-noise ratio per unit time and optimizing duty cycle in magnetic resonance spectroscopic imaging and/or for reducing chemical-shift artifacts at high magnetic fields. According to certain exemplary embodiments, imaging can thus be optimized.

Figure 1B:
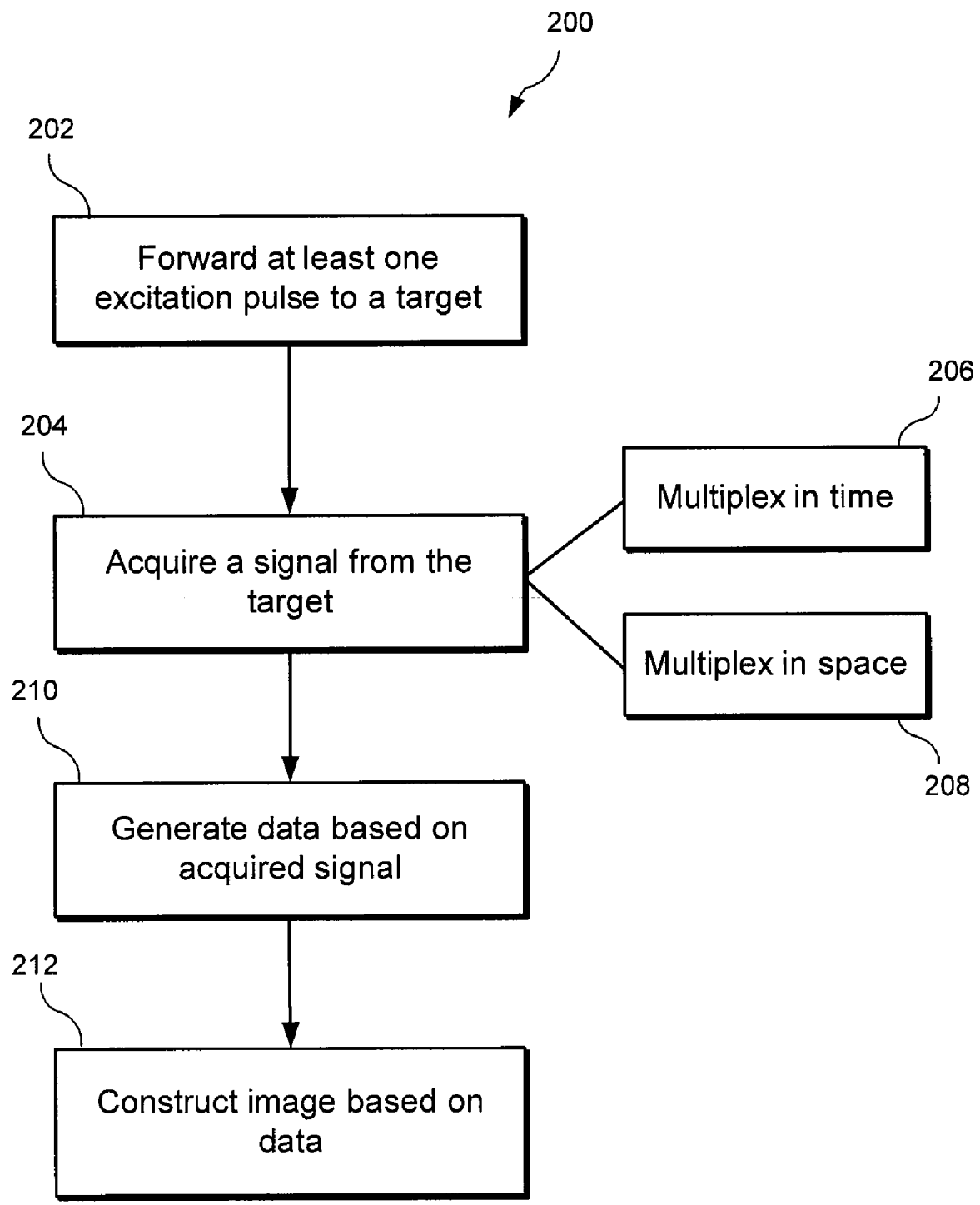
FIG. 1b is an exemplary flow diagram of an exemplary embodiment of a method according to the present invention.

FIG. 1a shows an exemplary embodiment of an MRSI apparatus 110 according to the present invention which may be used to implement or specifically configured/programmed to perform the method 10 described below with respect to FIGS. 1b and 1c.

As shown in FIG. 1a, at least one radio frequency ("RF") pulse 182 can be transmitted by an RF transmitter 150 of the MRSI apparatus 110 toward a target 180. The at least one RF pulse 182 can generate echoes 184 from the target 180, which may be received by an RF receiver 160 of the MRSI apparatus 110. In one exemplary embodiment, a single device, e.g., a transceiver, can be used as both an RF receiver 160 and an RF transmitter 150. The received echoes 184 (also referred to as acquired signal) may be processed by the processor 120 of the MRSI apparatus 110 using instructions 172 which, e.g., may be stored in memory 170. The data may be stored by the MRSI apparatus 110, for example, also in memory 170. The processor 120 can generate an image of the target 180 to be displayed, for example, on an output device 140. The exemplary embodiment of the MRSI apparatus 110 of FIG. 1a may also include an output device 140, such as a display, a printer for displaying, and/or printing the resulting image of the target 180. The exemplary MRSI apparatus 110 of FIG. 1a can further include an input device 130, for example, for sending instructions to the processor 120 to cause processor 120 to transmit the RF pulses 182, so as to process the data received from the echoes 184, and display the resulting image of the target 180.

Improving Exemplary SNR and Optimizing Duty Cycle

An exemplary embodiment of a method for improved SNR and acquisition efficiency in MRSI can be provided. In certain exemplary embodiments of the present invention, optimal SNR and acquisition efficiency for MRSI may be achieved simultaneously by multiplexing several slabs of several slices in space and time.

FIG. 1b illustrates a flow diagram of one exemplary embodiment of a method 200 for improving exemplary SNR and optimizing duty cycle. As shown in FIG. 1b, at least one excitation pulse is forwarded to a target [block 202]. A signal is acquired from the target resulting from the at least one excitation pulse [204]. The signal is acquired by multiplexing in time [block 206] and multiplexing in space [block 208]. Multiplexing in time may, in certain exemplary embodiments, comprises segmenting a field of view of the at least one portion of the target into a predetermined number of slabs that are acquired sequentially during each repetition time. Multiplexing in space may, in certain exemplary embodiments, comprise an acquisition of multiple voxels. Data may be generated based on the acquired signal [block 210] and an image may be constructed based on the data [block 212].

FIGS. 2a-2c provide schematic exemplary illustrations of multiplexing in time, space, and time and space for N=4 slices according to an exemplary embodiment of the present invention. FIG. 2a illustrates multiplexing in space with all slices 10, 12, 14, 16 used for each acquisition cycle ($T_C$) 18, 20, 22, 24 and where the repetition time (TR)=$TR_{opt}$. As shown, increasing the spatial coverage from single- to simultaneous multi-voxel acquisition can provide more spatial information at a similar SNR as determined by the voxel size and acquisition time While multiplexing in space can be optimal for SNR, it can be suboptimal in duty cycle ("DC"). FIG. 2b illustrates multiplexing in time with all $T_C$ values 18, 20, 22, 24 used per TR and with DC at approximately 100%. As shown in FIG. 2a, acquiring $T_C$-s for every TR, where each can be obtained from a different slice, 10, 12, 14, 16, can maximize the amount of information obtained per unit time by increasing the duty cycle ("DC") but can be less than optimal in SNR because TR>2·$T_{opt}$.

FIG. 2c illustrates an exemplary embodiment of multiplexing in both space and time with two slices per $T_C$ (slices 10 and 12 for $T_C$ 18 and 22, slices 14 and 16 for $T_C$ 20 and 24) and two $T_C$-s per $TR_{opt}$, with N·$T_C$/$T_{total}$~1 and TR=$TR_{opt}$. As shown in FIG. 2c, multiplexing in both space and time in accordance with exemplary embodiments provided herein can lead to improvements in both SNR and DC as compared with conventional techniques. For example, when more than one $T_C$ fits into $TR_{opt}$, slab-interleaving can be more efficient than either a multislice approach or a whole volume-of-interest ("VOI") per $TR_{opt}$ coverage. Reference is made to *Fast Proton Spectroscopic Imaging of Human Brain Using Multiple Spin-Echoes*, Duyn et al., Magn Reson Med 1993; 30(4): 409-414; *NMR Chemical Shift Imaging in Three Dimensions*, Brown et al., Proc Nat Acad USA 1982; 79:3523-3526; *Spatially Resolved High Resolution Spectroscopy by "Four Dimensional" NMR*, Maudsley et al., J Magn Reson 1983; 51:147-152; *Three-Dimensional Spectroscopic Imaging with Time-Varying Gradients*, Adalsteinsson et al., Magn Reson Med 1995; 33(4):461-466; *Volumetric Spectroscopic Imaging with Spiral-Based k-Space Trajectories*, Adalsteinsson et al., Magn Reson Med 1998; 39(6):889-898; *Three-Dimensional Echo-Planar MR Spectroscopic Imaging at Short Echo Times in the Human Brain*, Posse et al., Radiology 1994; 192(3):733-738; *Double-Echo Multislice Proton Spectroscopic Imaging using Hadamard slice encoding*, Dreher et al., Magn Reson Med 1994; 31(6):596-600; *3D Localized in vivo 1H Spectroscopy of Human Brain by Using a Hybrid of 1D-Hadamard with 2D-Chemical Shift Imaging*, Gonen et al., Magn Reson Med 1997; 37(5):644-650; and *3D Mutlivoxel Proton Spectroscopy of Human Brain using a Hybrid of $8^{th}$-order Hadamard Encoding with 2D Chemical Shift Imaging*, Gonen et al., Magn Reson Med 1998; 39(1):34-40, all incorporated herein by reference in their entireties. This advantage can increase with the number of slices and field strength, $B_0$. Exemplary results of such exemplary technique are described in the examples for a phantom and an in vivo human brain.

Multiplexing in Time, in Space, and in Time and Space

An $^1$H-MRSI sequence in accordance with an exemplary embodiment of the invention may yield the highest SNR per unit time from as many voxels as possible. To compare different sequences, the SNR as well as acquisition efficiency (e.g., data per unit time), may be considered. An "efficiency" parameter, η can be provided as shown in Equation 1 below, which includes both factors for comparing sequences:

$$\eta = \frac{SNR}{\text{effective time per slice}} = \frac{SNR \times N}{T_{total}}, \quad [1]$$

where $T_{total}$ is a total measurement time and N is a number of acquisitions (e.g., slices). Encoding along one direction, as described below, can emphasize the possibility of additional encodings of various types which may be applied in other orientations.

As may be appreciated from Equation 1 herein, sequences requiring extensive averaging, even if efficient in data collection, may not necessarily be optimal because the SNR value increases only as $(T_{total})^{1/2}$. Alternatively, η can be invariant with respect to the addition of slices when such addition requires more acquisition time, because N is inversely proportional to $T_{total}$. To compare different sequences, therefore, one of the parameters (e.g., $T_{total}$, SNR or N) should be kept constant.

MRSI sequences may generally differ in their TR, effective averaging, and duty cycle. The dependence of a voxel's signal, S, on the TR, for a given $T_1$, $T_{total}$ and flip angle φ, can be written as:

$$S \propto \frac{1-\exp(-TR/T_1)}{1-\exp(-TR/T_1)\cos(\phi)} \cdot \sqrt{\frac{T_{total}}{TR}} \sin(\phi) \quad [2]$$

where the first term can account for progressive saturation and the second term can account for N. A plot of S versus TR for the common angle φ=90°, shown in FIG. 3, indicates a broad maximum, e.g., a best SNR, may occur at a TR value of about:

$$TR=TR_{opt} \approx 1.2 T_1. \quad [3]$$

Figure 3:
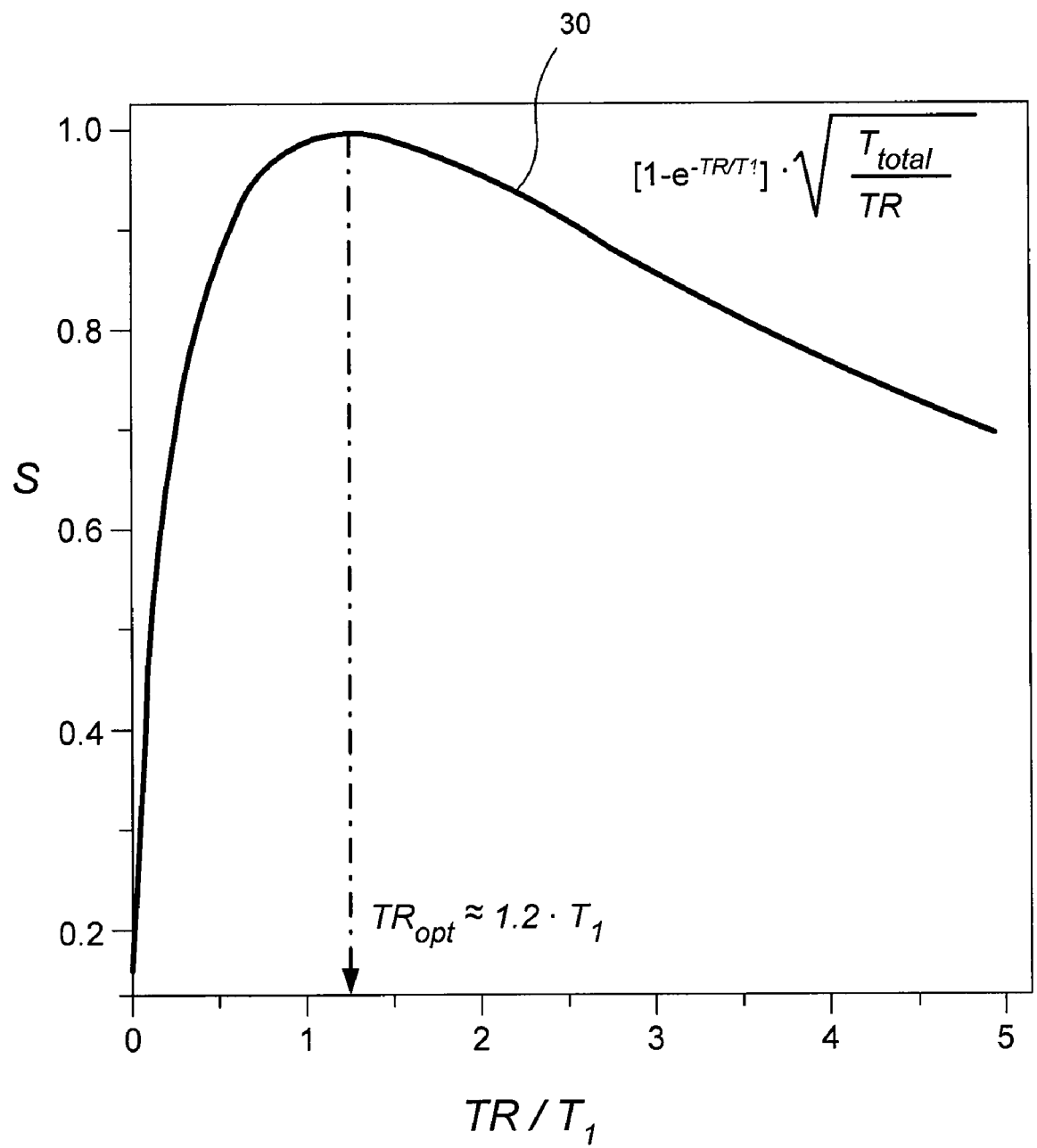
FIG. 3 illustrates a plot for a particular formulation in accordance with the exemplary embodiment of the present invention.

FIG. 3 illustrates a plot 30 of Equation 2 for φ=90° showing the dependence of the (normalized) signal strength, S, on the effective recycle time, TR. As shown, an optimum value of TR, $TR_{opt}$, can occur at TR≈1.2·$T_1$ Acquisition efficiency, which can be proportional to information per unit time, may be maximized when the receiver duty cycle approaches 100%, e.g.:

$$N \cdot T_C/T_{total} \rightarrow 1, \quad [4]$$

where $T_C$ can represent a single-acquisition cycle length.

Because $T_C$ may be generally less than or equal to $TR_{opt}$, multiplexing in time can maximize the DC by inserting as many $T_C$-s as will fit into each TR. However, more acquisitions may be needed, such that a value of TR=N·$T_C$ that is greater than $TR_{opt}$ can be used, as shown in FIG. 2b. This condition may satisfy Equation 4, but may not satisfy Equation 3. Thus, although the DC value can remain high, the SNR value may decrease as N (and TR) increase, which can result in a low value of η.

One exemplary way to circumvent such SNR deficiency described above is to multiplex in space, such as by collecting all N slices for each value of each TR=$TR_{opt}$, as shown in FIG. 2a Examples of such optimization can include, e.g., 3D chemical shift imaging (CSI) variants. However, because $T_C$ is less than $TR_{opt}$, an exemplary system may idle for a duration of ($TR_{opt}$−$T_C$) between acquisitions, as shown in FIG. 2a. This can lower the DC value, which may further lead to $T_{total}$=N·$TR_{opt}$ being greater than N·$T_C$. It may thereby take twice as long to cover the same VOI as compared with a technique that multiplexes in time as shown, e.g., in FIG. 2b. For example, if a system was pulsed at TR=$T_C$, and not at $T_{opt}$, to address this, it may sustain an SNR loss according to Equation 3. Because both conditions may not be met simultaneously, multiplexing in space can be inherently suboptimal in either its SNR or DC, which may be reflected in a lower value of η, as described below.

In exemplary embodiments of the present invention, deficiencies of multiplexing in either time or space can be avoided by multiplexing in both time and space simultaneously. For example, inter-$T_C$ "idling" may be avoided by segmenting the VOI into M sequentially interleaved (multiplexed in time) slabs (multiplexed in space), with M<N, as shown in FIG. 2c, such that:

$$M \cdot Tc = TR_{opt} \text{ i.e., } M = \text{int}\left(\frac{TR_{opt}}{Tc}\right) \quad [5]$$

This exemplary strategy can facilitate a retention of an optimal TR value when DC is approximately 100%. The number of simultaneously acquired (multiplexed in space) slices, m, in each slab which can yield a total of N such slices in the VOI can be expressed by:

$$m=\text{int}(N/M), \quad [6]$$

as shown in FIG. 2c.

To apply Equation 1 to the three sequences of FIGS. 2a, 2b, and 2c, the SNR obtained with $TR_{opt}$ may be arbitrarily set equal to unity, and a value of η can be calculated for N=4. For multiplexing in space (as shown, e.g., in FIG. 2a), η=1/$T_C$; for multiplexing in time (as shown, e.g., in FIG. 2b), η<1/$T_C$ due to non-optimal values of TR; and for multiplexing in time and space (as shown, e.g., in FIG. 2c), η=$2^{1/2}$/$T_C$, which can demonstrate the advantage of such time and space multiplexing as compared with multiplexing in space or time alone.

Practical Exemplary Considerations: $B_0$ and the Number of Slabs—M

The exemplary number of slabs, M, prescribed by Equation 5, can be derived from $TR_{opt}$ and $T_C$ which may depend on the echo time (TE) and $T_2^*$. Because $T_1$-s of the main brain metabolites may be nearly field-independent for magnetic fields ranging from about 1.5 to 7.0 T, $TR_{opt}$ may be approximately 1.6 s (cf. Equation 2) across more than 2 octaves of $B_0$ values. Values of $T_2^*$, however, may be approximately inversely related to the value of $B_0$ at 1.5, 3.0 and 7.0 T. Consequently, according to Equation 5, M may increase approximately linearly with $B_0$.

For example, at 1.5 T, in vivo 5·$T_2^*$(NAA) may require approximately 1 s signal acquisition for sufficient spectral resolution. Adding a value for TE of about 135 ms and effects of water suppression can bring the $T_C$ value to about 1.2 s. For example, if $TR_{opt}$ is approximately 1.6 s, M=int(1.6/1.3)=1 according to Equation 5, and multiplexing in space can be optimal in SNR. At a magnetic field of 3.0 T, however, the $T_2^*$ can be reduced by one-half, which may enable a reduction in $T_C$ to about 800 ms. Since the value of $TR_{opt}$ remains 1.6 s, M=2 and multiplexing in space and time can become optimal. This possible advantage may increase with an increasing value of $B_0$ because $T_2^*$ (and $T_C$) decrease. Increasing $B_0$ may, in some specific scenarios such as with use of spatially-selective excitation, lead to metabolite localization errors from different chemical shift displacements ("CSDs") and is addressed herein with respect to reducing such CSDs.

For typical values of TRs and $T_C$S which may be used in MRS analyses, the value of M may typically be less than or equal to about 6, as suggested by Equation 5. A reasonable choice for N can yield values of m-s, from Equation 6, that are powers of 2. This may, in some exemplary embodiments, be almost automatic because, based on sensitivity considerations, voxel sizes may be about 1 cm³, such that about 8-12 voxels may fit in any direction in a human brain. Hadamard spectroscopic imaging (HSI) may be employed in that direction to provide better slice profiles and reduced voxel bleed for few partitions (e.g., less than or equal to about 8), as described by Gonen et al. in 3D *Localized In Vivo 1H Spectroscopy of Human Brain by Using a Hybrid of 1D-Hadamard with 2D-Chemical Shift Imaging*, Magn Reson Med 1997; 37(5):644-650, incorporated herein by reference in its entirety.

Thus, as described herein, maximum acquisition duty-cycle may be obtained by multiplexing in time several single-slices for each repetition time ("TR") and optimal SNR can be achieved by encoding the entire volume-of-interest ("VOI") for each TR. For example, coverage of common VOIs in 3D proton MRSI in a human brain may typically use 8 or more slices, at 3 T or higher magnetic fields, such that two or more slabs can fit into the optimal TR ~1.6 s. Because four or fewer slices would typically fit in each such slab, Hadamard encoding may be favored in that direction for slice profile reasons. For a particular examination length, the exemplary techniques described herein with respect to exemplary embodiments may provide approximately twice as many voxels at 3 T, each voxel having the same SNR and size, as compared with conventional 3-dimensional chemical shift imaging techniques. This gain can increase for more extensive spatial coverage or higher fields.

To make MRSI feasible for clinical use, it may be desirable to obtain the best SNR per unit time from as many voxels as possible. The SNR of each voxel can depend on its volume and the time available for acquisition. Thus, when the target resolution and measurement time have been selected, the SNR can be improved by either (i) approaching or meeting that limit; or (ii) increasing the acquisition efficiency, e.g., the spatial coverage. Exemplary embodiments of the present invention can provide techniques for achieving such optimal data for various values of $B_0$, through associated $T_1$ and $T_2^*$ values.

As discussed herein, two conventional multivoxel techniques (e.g., multiplexing only in space or only in time) may be inherently suboptimal. Slice interleaving may provide suboptimal SNR values because: (i) the effective TR may not be optimal; and (ii) not all time is used to average all slices. Further, the various multiplexing in space methods can be suboptimal with respect to their duty-cycle, which can result in fewer voxels per unit time despite an optimal SNR. Exemplary embodiments of the present invention can provide an effective technique which utilizes the positive features of these two conventional techniques, as shown in FIG. 2c.

Using such a hybrid approach (with both multiplexing in space and multiplexing in time), for equal time and voxel sizes, the value of η can be largest when using a multi-slab approach (see Table 1, below). For equal coverage (e.g., N=8 slices), multiplexing in time+space can yield an SNR value which exceeds that obtained by multiplexing in time alone by almost a factor of two (see Table 2, below). Further, although the SNR obtained by multiplexing in time+space may be comparable to that achieved by multiplexing in space alone, the duty cycle value yields twice as many slices in the same time when multiplexing in both time+space.

Multiplexing in time+space can offer two additional advantages over other high-field acquisition schemes. First, since only a subsection of the VOI is excited in each $T_C$, second, for a fixed radio-frequency strength, $B_1$, the slice-selection gradient, G, can be increased to proportionally decrease the chemical shift offset of the VOI between two peaks which may be $\Delta\omega_{p-p}$ Hz apart. Such chemical shift offset, Δx, can be expressed as:

$$\Delta x = \Delta\omega_{p-p}/G. \quad [7]$$

Because the VOI may be segmented into M (thinner) slabs (as shown, e.g., in FIGS. 2a and 2c), G can be increased by an amount N/M (which may be greater than or equal to 2) at a fixed value of $B_1$. Thus, Δx can be more than halved, as indicated by Equation 7. Maintaining a constant value of $B_1$ at higher fields may require more (peak) instantaneous RF power, but the SINC-like envelope of the Hadamard pulses can have a relatively modest impact on the overall SAR. Further, this improvement in Δx can be greater for a fixed VOI as M increases further, e.g., for field strengths of 4, 7, or 9.4 T and beyond, based on $T_2^*$ and, consequently, $T_C$ contraction. The multi-slab approach disclosed in exemplary embodiments herein, therefore, may be suited to $^1$H-MRSI applications at high $B_0$ values.

Exemplary embodiments of the present invention can also integrate with 3D fast k-space scanning $^1$H-MRSI techniques, such as spirals, as discussed in *Three-Dimensional Spectroscopic Imaging with Time-Varying Gradients*, Adalsteinsson et al., Magn Reson Med 1995; 33(4):461-466; *Volumetric Spectroscopic Imaging with Spiral-Based k-Space Trajectories*, Adalsteinsson et al., Magn Reson Med 1998; 39(6):889-898, incorporated herein by reference in their entireties, EPSI, as discussed in *Three-Dimensional Echo-Planar MR Spectroscopic Imaging at Short Echo Times in the Human Brain*, Posse et al., Radiology 1994; 192(3):733-738 and *Proton Echo-Planar Spectroscopic Imaging with Highly Effective Outer Volume Suppression using Combined Presaturation and Spatially Selective Echo Dephasing*, Chu et al, Magn Reson Med 2003; 49(5):817-821, herein incorporated by reference in their entireties, or spectroscopic RARE, U-FLARE, and GRASE, as discussed in *Fast Proton Spectroscopic Imaging with High Signal-to-Noise Ratio: Spectroscopic RARE*, Dreher, Magn Reson Med 2002; 47(3):523-528; *A Fast Variant of (1)H Spectroscopic U-FLARE Imaging using Adjusted Chemical Shift Phase Encoding*, Ebel et al., J Magn Reson 2000; 142(2):241-253; and *A New Method for Fast Proton Spectroscopic Imaging: Spectroscopic GRASE*, Dreher, Magn Med 2000; 44(5):668-672, incorporated herein by reference in their entireties. Since these techniques can cover the entire VOI for each $T_C$, they can be equivalent to "multiplexing in space" and thus may be susceptible to the "Macovski SNR limit." Using CSI for phase-encoding, these techniques currently employ a single slab (e.g., M=1) to maximize the number of slices in the VOI and thereby reduce "voxel bleed", discussed in *Practical Applications of Chemical Shift Imaging*, Brown, NMR Biomed 1992; 5(5):238-243, incorporated herein by reference in its entirety. Furthermore, while such exemplary techniques may be data intensive per-shot, they can be suboptimal with respect to DC, since the corresponding $T_C$ value is less than $TR=TR_{opt}$. Such inefficiency can be exacerbated at higher values of $B_0$, where RF power and current gradient hardware and physiological performance limitations may not meet expanded spectral bandwidth that may be required in a single shot. Integrating such fast scans into the "multiplexing in time+space" approach, e.g., segmenting the VOI into slabs according to Equation 5, can be straightforward, can address the efficiency issue of these techniques, and may help to overcome RF and SAR limitations which may be present over more extensive VOI sizes.

The topic of sensitivity in interleaved-2D versus 3D coverage for MRI studies has been described, e.g., in *2D Multi-slice and 3D MRI Sequences are often Equally Sensitive*, Johnson et al., Magn Reson Med 1999; 41(4):824-828, incorporated herein by reference in its entirety. Based on formulations similar to those presented in Equations 2 and 4 herein, it was observed that the SNR values of the two techniques may be indistinguishable when the TR values also were indistinguishable, or when the TR value was less than $T_1$ and an Ernst angle was used. While both conditions can be met in MRI, where in general $T_C \ll T_1$, neither condition may be generally practical in MRS analyses, especially for 3D $^1$H-MRS. It was further observed that 3D MRI coverage can often provide a better SNR value, whereas the 2D variants, due to $B_1$ and gradient strength limitations, may provide better slice profiles.

Exemplary embodiments of the present invention can utilize pulse-sequences, e.g., PRESS or STEAM, which may commonly be used for MRSI analyses, and thus can exhibit their performance profiles. To increase η, more acquisitions can be compressed into each TR. This can increase the number of radio-frequency pulses and, consequently, the specific absorption rate ("SAR"). For example, at 3 T, the SAR for two slabs per $TR_{opt}$ was observed to be within the FDA approved value of 3.2 W·Kg$^{-1}$. At higher magnetic fields, however, where more slabs could fit into $TR_{opt}$, the increased power per pulse required may limit the number of slabs per TR, e.g., the level of efficiency which may be obtained.

Thus, exemplary embodiments of the present invention can account for tradeoffs between the SNR and DC of various conventional MRSI acquisition techniques and provide techniques for combining and optimizing them. This may be desirable in view of increases in field strengths of modern imagers to 3, 4, or 7 T and beyond. While the MR signal strength and $T_1$ values may increase with $B_0$, the $T_2^*$ values can proportionally decrease. Such changes can be utilized to facilitate an operation at an optimal SNR and DC for a particular choice of voxel-size (resolution), number of slices (spatial coverage), and/or $B_0$ value. Exemplary embodiments of the present invention can also provide several collateral advantages, such as the ability to increase slice-selective gradients to improve voxel profiles, reduce chemical-shift artifacts, and/or allow a lower value of $B_1$, each of which may be desirable for high and ultra-high magnetic field analyses.

Example for Improving SNR and Optimizing DC

All experiments were performed in a 3.0 T Magnetom Trio (Siemens AG, Erlangen Germany), with a TEM 3000 head coil (MRInstuments, St. Paul, Minn.) on: (i) a 1 L sphere containing physiological concentration in water of the main brain metabolites; and (ii) the brain of a healthy 52 year old female volunteer.

For VOI positioning, 15 axial, sagittal and coronal T1-weighted spin-echo (TE/TR=15/450 ms) 7.5 mm thick MRI slices were obtained at 240×240 mm$^2$ FOV. Auto-shimming was then performed to yield 2.0±0.5 Hz voxel metabolite linewidths in the phantom, and 6.0±1.0 Hz voxel metabolite linewidths in vivo. The three 3D $^1$H-MRSI schemes illustrated in FIGS. 2a-2c were compared as follows:

1. Time-multiplexed multi-slice, similar to that shown in FIG. 2b. N=8 slices 0.75 s, cm (superior-inferior), each, were applied sequentially under 9 mT/m. A $T_C$=800 ms led to a TR of 6.4 s.
2. Space-multiplexed, similar to that shown in FIG. 2a. At $TR=TR_{opt}$=1.6 s, only N=4$_{SI}$ slices fit in $T_{total}$. To retain voxel size, a 3$_{SI}$ cm VOI was encoded under 3 mT/m with 4$^{th}$ order HSI, which may be preferable for <8 partition based on slice profile. Protocol for space multiplexing was substantially as described in 3D Localized in vivo 1H *Spectroscopy of Human Brain by Using a Hybrid of 1D-Hadamard with 2D-Chemical Shift Imaging*, Gonen et al., Magn Reson Med 1997; 37(5):644-650; *3D Multivoxel Proton Spectroscopy of Human Brain using a Hybrid of 8$^{th}$-Order Hadamard Encoding with 2D Chemical Shift Imaging*, Gonen et al., Magn Reson Med 1998; 39(1):34-40; and *Hybrid Three Dimensional (1D-Hadamard, 2D-Chemical Shift Imaging) Phosphorus Localized Spectroscopy of Phantom and Human Brain*, Gonen et al., Magn Reson Med 1995; 33(3):300-308, all incorporated herein by reference in their entirety.
3. Time+space multiplexed, similar to that shown in FIG. 2c. With $T_C$~800 ms and $TR_{opt}$=1.6 s, based on Equation 5, $M=T_{opt}/T_C=2$ slabs, 3$_{SI}$ cm each, were applied sequentially, under 3 mT·M$^{-1}$. The m=8/2=4 slices per slab were also defined with 4$^{th}$ order HSI.

All experiments featured a 12 cm left-right (LR)×12 cm anterior-posterior (AP)×6$_{SI}$ (or 3$_{SI}$) cm FOV encoded with a 16$_{AP}$×16$_{LR}$×8 (or 4)$_{IS}$ matrix. The VOIs were 8$_{LR}$×10$_{AP}$×6$_{SI}$ (or 3$_{SI}$) cm$^3$, excited using TE=135 ms PRESS, for a nominal 0.42 cm$^3$ voxels. This choice of voxel size and TE were selected to provide an SNR in the range of about 10-100, differences amongst which can be easily compared visually. The encoding resulted in 760 voxels within the VOI in experiment 2 and 1520 voxels within the VOI in experiments 1 and 3, above. At 500 ms acquisition, $T_C$ was 800 ms and $T_{total}$ was 27.3 minutes.

Table 1 summarizes the experimental parameters together with corresponding expected SNR and η values.

TABLE 1

| Multiplexing in: | Time | Space | Time + Space |
|---|---|---|---|
| $T_{total}$ | 27.3 min | 27.3 min | 27.3 min |
| Matrix | 16$_{AP}$ × 16$_{LR}$ × 8$_{IS}$ | 16$_{AP}$ × 16$_{LR}$ × 4$_{IS}$ | 16$_{AP}$ × 16$_{LR}$ × 8$_{IS}$ |
| Effective TR | 6.4 sec | 1.6 sec | 1.6 sec |
| Effective averages | 1 | 4 | 4 |
| Gradient used | 9 mT/m | 3 mT/m | 3 mT/m |
| N Slices (thickness) | 8 (0.75 cm) | 4 (0.75 cm) | 8 (0.75 cm) |
| SNR* | <1 | 2 | 2 |
| η | <1/$T_C$ | 1/$T_C$ | 2/$T_C$ |

*SNR defined as "1" for one average and TR = $TR_{opt}$

Table 1 illustrates exemplary parameters used in the three exemplary experiments together with anticipated values of SNR and η. Note that although multiplexing in space has the same SNR as multiplexing in time and space, multiplexing in time and space has twice as many slices for the same total acquisition time as multiplexing in space alone. Both techniques provide similar SNR values. Accordingly, multiplexing in time and space can have an improved SNR compared with multiplexing in time alone and also has a doubled value for η.

Residual water was removed from the MRS data in the time domain, as described in *Improved Solvent Suppression in One-and Two-Dimensional NMR Spectra by Convolution of the Time Domain Data*, Marion et al., J Magn Reson 1989; 84:425-430, incorporated herein by reference in its entirety. The signals were then apodized with a 3 Hz Lorentzian, voxel-shifted to align the CSI grid with the NAA VOI, and Fourier transformed in two spatial and the spectral directions. No spatial or spectral filters were used to emphasize SNR performance in the comparisons. Data multiplexed in space and time+space were Hadamard transformed along that spatial direction. Automatic frequency and zero-order phase correction were made, referencing NAA and Cr peaks in each voxel, as described in *Multivoxel 3D Proton Spectroscopy in the Brain at 1.5 versus 3.0 T: Signal-to-Noise Ratio and Resolution Comparison*, Gonen et al., AJNR Am J Neuroradiol 2001; 22(9):1727-1731, incorporated herein by reference in its entirety. Relative levels of the i$^{th}$ (e.g., NAA, Cr, or Cho) metabolite in the $j^{th}$ (e.g., j=1 . . . 1520) voxel, were estimated from their peak areas, $S_{ij}$, using parametric spectral modeling and least-squares optimization as described, e.g., in *Automated Spectral Analysis III: Application to in vivo Proton MR Spectroscopy and Spectroscopic Imaging*, Soher et al., Magn Reson Med 1998; 40(6):822-831, incorporated herein by reference in its entirety. $S_{ij}$ s were converted into peak-heights, $h_{ij}$, $=S_{ij} \times T_2^i$, as described in *The NMR Receiver: A Description and Analysis of Design*, Hoult, Prog in NMR Spec 1978; 12:41-77, incorporated herein by reference in its entirety, and divided by the root mean square ("rms") noise from a signal-free spectral region for the SNR, as described in *Principles of Nuclear Magnetic Resonance in One and Two Dimensions*, Ernst et al., The International Series of Monographs on Chemistry, Oxford: Clarendon Press; 1987, p. 152, incorporated herein by reference in its entirety, and *Multivoxel 3D Proton Spectroscopy in the Brain at 1.5 versus 3.0 T: Signal-to-Noise Ratio and Resolution Comparison*, Gonen et al., AJNR Am J Neuroradiol 2001; 22(9):1727-1731, incorporated herein by reference in its entirety.

Experiments 1, 2, and 3, described herein above, were performed on the phantom sample consecutively to ensure common VOI position, shim and gain parameters. Exemplary spectra are shown in FIGS. 4a-4d. FIG. 4d illustrates an axial $T_1$-weighted MRI image 40 obtained from a phantom sample superimposed with the $^1$H-MRSI FOV, VOI and three sample 0.42 cm$^3$ voxels. FIGS. 4a-4c illustrate $^1$H Spectra from these voxels from 3 consecutive 27 min. experiments multiplexed in time, shown at 42, space, shown at 44, and both time+space, shown at 46. All spectra are shown on a common chemical shift scale, normalized to equal NAA signal peak height. Inserts in these spectra are baseline noise (×5) to emphasize SNR. As shown, multiplexing in space and time+space are similar in SNR, but the latter yielded×2 slices and both are approximately twice as effective as multiplexing in time alone.

Figure 5C:
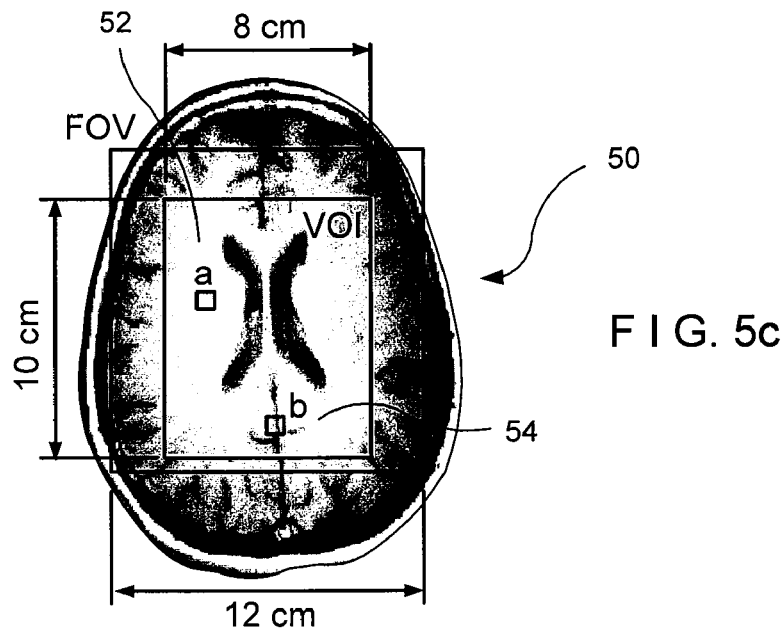
FIG. 5c illustrates an axial T1-weighted MRI from a brain superimposed with MRSI FOV and VOI in accordance with the exemplary embodiment of the present invention.
Figure 5A:
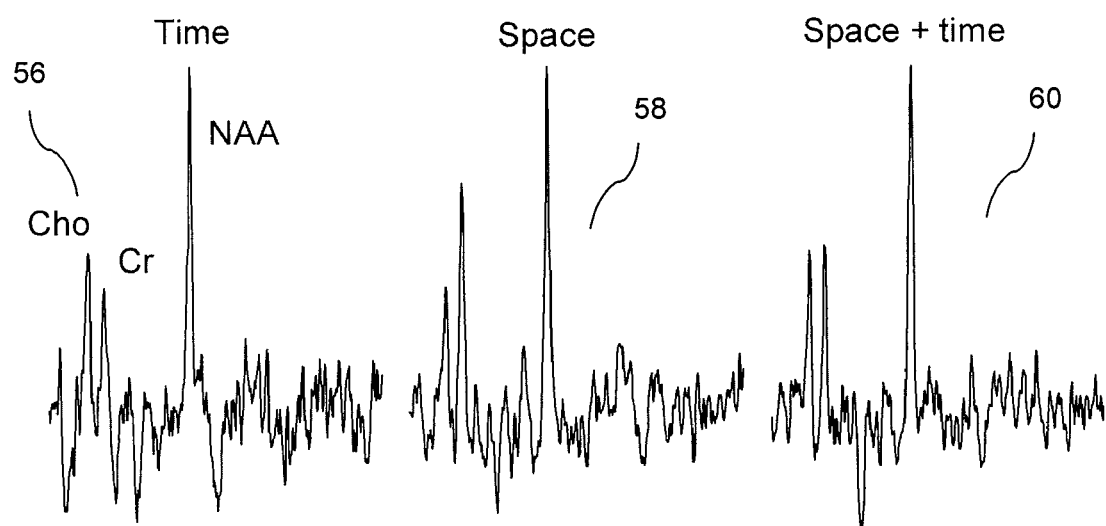
FIG. 5a illustrates a $^1$H Spectra for two representative voxels from a first experiment multiplexing in time, space, and both time and space in accordance with a particular exemplary embodiment of the present invention.
Figure 5B:
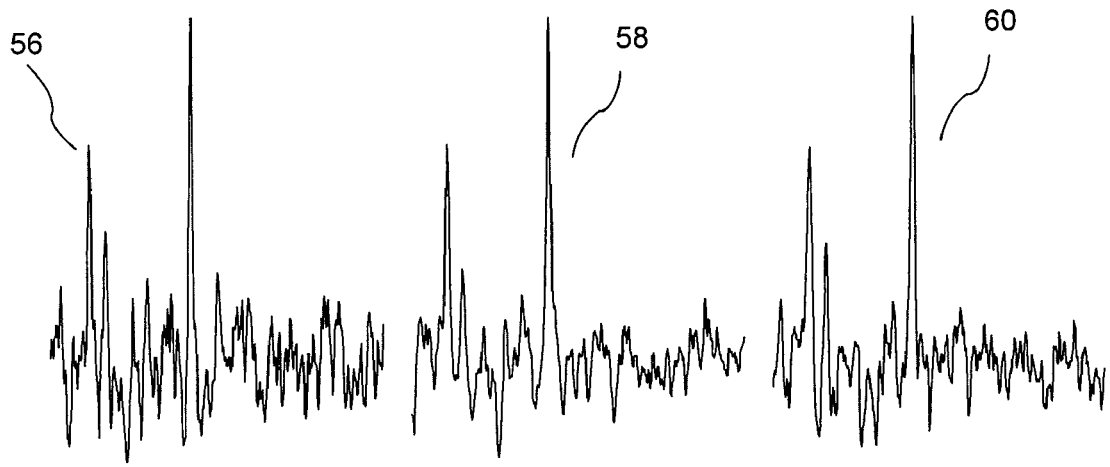
FIG. 5b illustrates a $^1$H Spectra for two representative voxels from a second experiment multiplexing in time, space, and both time and space in accordance with another exemplary embodiment of the present invention.

The same three experiments were repeated consecutively in the brain of a healthy volunteer. Examples of the spectra are shown in FIGS. 5a-5c, and the observed SNR values from the 760 or 1520 voxels within the VOI for each metabolite are shown in Table 2. FIG. 5c illustrates an axial $T_1$-weighted MRI 50 from the brain of a volunteer superimposed with the MRSI FOV and VOI. FIGS. 5a and 5b show $^1$H Spectra from two (0.75 cm)$^3$=0.42 cm$^3$ representative voxels, from primarily gray and white matter regions labeled 52 and 54 on FIG. 5c, from 3 consecutive experiments ($T_{total}$=27 min.) multiplexing in time, shown at 56, space, shown at 58, and both time+space, shown at 60. All spectra are shown on a common chemical shift scale and normalized to equal NAA peak height to emphasize SNR. The space and time+space multiplexed spectra are similar in SNR (the latter yielded twice as many slices) and both are about twice as effective as multiplexing in time alone.

The in vivo SNR values of the major metabolites were observed to be similar for multiplexing in time+space and in space alone, as demonstrated in the phantom sample. Both multiplexing techniques appear to be about twice as effective as multiplexing in time alone, as suggested buy the data in Table 1.

Metabolite SNR values from the 760 voxels of the 4 slices multiplexed in space, or 1040 voxels from the 8 slices multiplexed in time and in time+space, are provided in Table 2. SNR values for the three main metabolites may be preferable for multiplexing in time+space and in space alone, as both techniques may be about twice as effective as compared with multiplexing in time alone, as expected after substituting the phantom $T_1$ values (cf Table 1).

TABLE 2

| Multiplexing in: | | Time | Space | Time + space |
|---|---|---|---|---|
| Sample | Metabolite | N = 1520 | N = 760 | N = 1520 |
| Phantom | NAA | 47.8 ± 3.5 | 92.6 ± 6.7 | 100 ± 8.1 |
|  | Cho | 18.3 ± 2.1 | 39.8 ± 3.2 | 46.4 ± 2.9 |
|  | Cr | 26.6 ± 2.5 | 57.2 ± 3.6 | 64.0 ± 4.3 |
| In vivo brain | NAA | 56.3 ± 15.3 | 97.1 ± 21.2 | 100 ± 20.8 |
|  | Cho | 25.6 ± 7.4 | 49.8 ± 12.5 | 47.3 ± 10.2 |
|  | Cr | 24.7 ± 7.6 | 47.1 ± 11.8 | 44.0 ± 12.2 |

Table 2 shows average (±one standard deviation) SNR values [e.g., peak-height/rms-noise], for three main $^1$H metabolites for each of the three multiplexing methods shown in Table 1, for both the phantom sample and in vivo measurements (see FIGS. 4 and 5) in a 27 min. acquisition time. N indicates the number of (0.75)$^3$=0.42 cm$^3$ voxels used in the analyses. All exemplary SNR values are scaled relative to the value for NAA in the time+space multiplexed experiment, which is arbitrarily set at 100. The SNR values are similar for multiplexing in space alone and in time+space, although the latter yielded twice as many voxels in the given acquisition time. Both sets of SNR values exceed that obtained by multiplexing in time alone.

Reducing Chemical Shift Artifacts

In further exemplary embodiments of the present invention, techniques can be provided for reducing chemical shift artifacts in MRSI at high (e.g., 3 T and 7 T) magnetic fields. Exemplary embodiments of the present invention comprise two cooperative techniques which can reduce the value of $B_1$ needed to cover a given FOV: Multi-slab excitation and RF pulse cascades. The first technique (multi-slab excitation) can reduce $B_1$ by a factor of about 2 to 4, whereas the second technique (RF pulse cascades) can reduce $B_1$ by a further factor of about 2 to 8. An exemplary combination of the first and second techniques can enable a nearly tenfold increase in gradient strength, which may be sufficient to lower a chemical-shift-displacement ("CSD") to less than about 0.02 or 0.05 cm/ppm at 3 T or 7 T.

Finite bandwidth slice-selective RF pulses used in $^1$H-MRSI can be positioned relative to a magnet center by a frequency shift, $\omega_{off}$, from carrier, $\omega_0$, under a gradient, $G_r$. Each selective pulse may excite only spins whose resonance frequency (e.g., based on chemical shift and gradient strength at that position) falls within its bandwidth, e.g.:

$$\omega_0+\omega_{off}-BW/2 \leq \gamma \cdot B_0(1-\sigma_i)+\gamma \cdot G \cdot r \leq \omega_0+\omega_{off}+BW/2, \qquad [8]$$

$$\omega_{min} \leq \gamma \cdot G \cdot r - \Delta\omega_i \leq \omega_{max}, \qquad [9]$$

where $\sigma_i$ can represent a chemical shift of species i (in ppm) and $\Delta\omega_i$ can represent a corresponding actual frequency offset from $\omega_0$.

Dividing Equations 8 and 9 by $\gamma \cdot G$ and applying the relationships $\omega=\gamma \cdot G \cdot r$ and $\Delta\omega_i=\gamma \cdot G \cdot \Delta r_i$ yields the following expressions:

$$r_{min} \leq r - \Delta r_i \leq r_{max}, \qquad [10]$$

$$r_{min} + \Delta r_i \leq r \leq r_{max} + \Delta r_i, \qquad [11]$$

e.g., a slice position is displaced by a different amount, $\Delta r_i$, for different values of $\sigma_i$. For example, at 7 T the 1.2 ppm (e.g., $\Delta\omega$=360 Hz) chemical shift between N-acetylaspartate (NAA) and choline (Cho), under $G_r$=1 mT/m (~420 Hz/cm) yields a relative CSD $\Delta r \approx 9$ mm.

The shape of the human head combined with the sensitivity of $^1$H-MRS at $B_0$ values of 3 T to 7 T using approximately 30 min. acquisition times suggests a selection of N=4 to 12 slices across the brain for imaging. Hadamard spectroscopic imaging may be a preferable localization technique when using such few slices, as discussed in 3*D Localized in vivo 1H Spectroscopy of Human Brain by Using a Hybrid of 1D-Hadamard with 2D-Chemical Shift Imaging*, Gonen et al., Magn Reson Med 1997; 37(5):644-650, herein incorporated by reference in its entirety. HSI pulses may be synthesized by superposition of $2^N$ (e.g., N integer) frequency-shifted SINCs of 0°/180° relative phases, according to different rows of the $N^{th}$ order Hadamard matrix, as discussed in *Transverse Hadamard Spectroscopic Imaging*, Goelman et al., J Magn Reson 1990; 89:437-454, herein incorporated by reference in its entirety. However, this technique may require a $B_1$ value that is N times greater than that for a single SINC. Two exemplary approaches for lowering such prohibitive RF power needs are described below.

Multi-Slab Acquisition

A particular exemplary embodiment for reducing chemical shift artifact in, for example, Hadamard-encoded MRSI at high magnetic fields, comprises multi-slab acquisition. As discussed above, an optimal signal-to-noise ratio per unit time ("SNR") and receiver duty cycle may be achieved by multiplexing acquisition in both space and time. This can be done, for example, by segmenting the FOV into M slabs that are acquired sequentially during each TR, as shown in FIG. 6. For example, FIG. 6 illustrates multiplexing several slabs 62, 64 (e.g., M=2), one per $T_C$ within each TR. Each slab is encoded with $m=2^{nd}$ order HSI for 4 slices 66, 68, 70, 72 total in the VOI at optimal acquisition efficiency. The HSI slices in each pulse are separated in space to obtain improved profiles, as discussed at *Reducing Voxel Bleed in Hadamard-Encoded MRI and MRS*, Goelman et al., Magn Reson Med 2006; 55(6):1460-1465, incorporated herein by reference in its entirety. The first $TR_1$, on top encodes [0°, 0°] relative transverse phases; the second, $TR_2$, encodes [0°, π] phases, corresponding to the [1, 1] and [1, −1] of a $2^{nd}$ order Hadamard matrix.

The number of slabs used for this procedure may be:

$$M = TR_{opt}/T_C,  \qquad [12]$$

where $TR_{opt}$, which can depend on $T_1$, is approximately 1.6 s between 1.5 T and 7.0 T and the cycle-time, $T_C$, can represent the duration of water and outer-volume suppression, selective excitation and digitization, and may typically be between about 500 to 750 ms at 3 T. For N slices being used to cover the FOV, m=N/M of them can fit within each slab, as shown in FIG. 6. Because the slabs are thinner than the FOV, each slab may preferably utilize a proportionally smaller value of $B_1$ per given gradient strength, e.g.:

$$B_1 \propto 1/M.  \qquad [13]$$

Because $T_1$ and $T_2^*$ relaxation times reported for brain metabolites at 3 T and higher fields can indicate the use of M=2-4 slabs of m=N/M=2-4 slices each, localization across such slabs may favor HSI based on a more desirable point-spread-function.

Pulse Cascading in Multi-Slice HSI

Figure 1C:
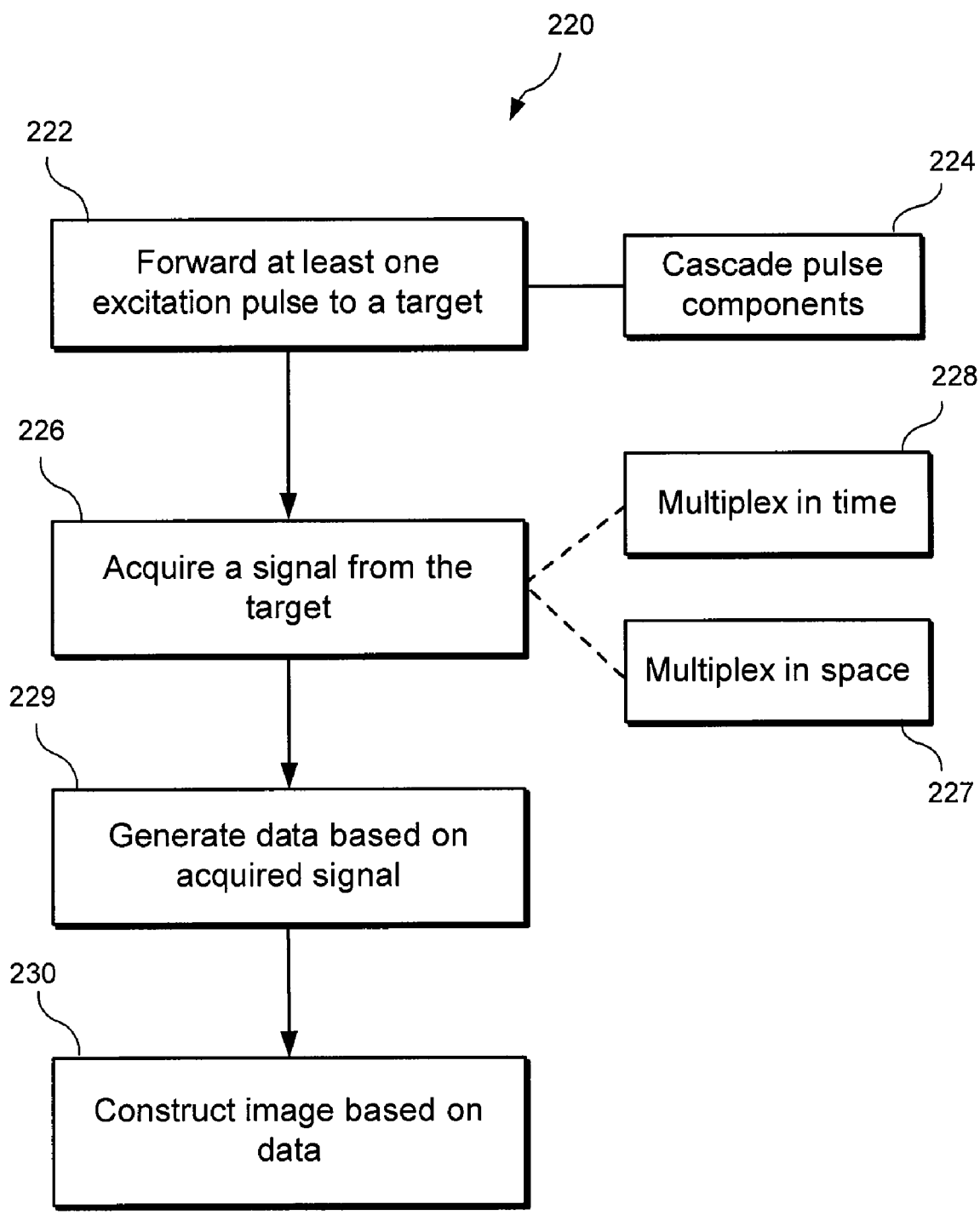
FIG. 1c is an exemplary flow diagram of another exemplary embodiment of a method according to the present invention.

FIG. 1c illustrates a flow diagram of one exemplary embodiment of a method 220 for reducing chemical shift artifact in, for example, Hadamard-encoded MRSI at high magnetic fields, comprises pulse cascading. As shown in FIG. 1c, at least one excitation pulse is forwarded to the target [block 222]. In the exemplary embodiment, the at least one excitation pulse comprises a series of Hadamard pulse components. The pulse components are cascaded [block 224]. A signal resulting from the at least one excitation pulse is acquired [block 226]. In some embodiments, the signal is acquired by multiplexing in space [block 227] and multiplexing in time [block 228]. Data may be generated based on the acquired signal [block 229] and an image may be constructed based on the data [block 230].

Linear superposition of N single-slice SINCs as shown, e.g., 74 in FIG. 7a, described below, may require an RF pulse bandwidth that is N times larger than that of each of its individual components. In certain exemplary embodiments, to maintain the same flip-angle, therefore, the peak $B_1$ can be increased N-fold as shown, e.g., 76 in FIG. 7a. However, smaller $B_1$ values which may be available at higher field strengths may restrict the bandwidth available for pulses. To keep the same FOV size, therefore, in an exemplary embodiment, the slice-select gradient may be reduced proportionally as shown, e.g., 78 in FIG. 7a, which can increase the CSDs that may already be undesirably high due to a higher $B_0$ value.

Figure 7A:
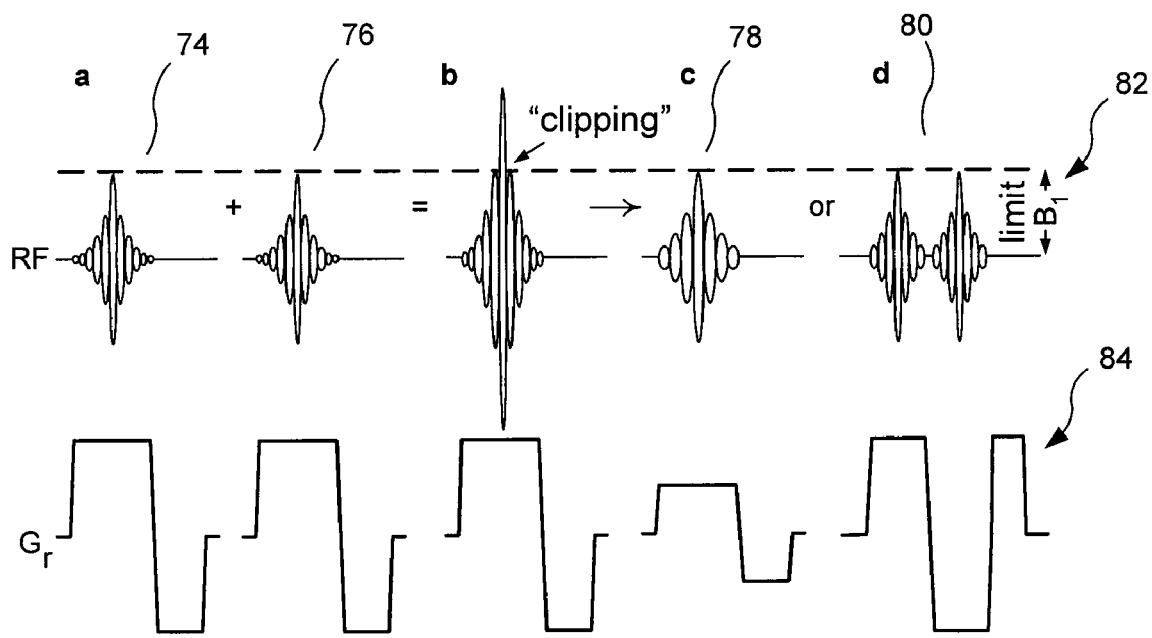
FIG. 7a illustrates a schematic diagram of radio frequency and gradient waveforms in accordance with the exemplary embodiment of the present invention.

To address this BW versus CSD conflict, single-slice components of the HSI pulses can be sequentially "played out" (e.g., cascaded) rather than being superpositioned as shown, e.g., 80 in FIG. 7a. This technique can reduce a required peak value of $B_1$ by the number of shifts in the cascade, m', e.g.:

$$B_1 \propto 1/m'.  \qquad [14]$$

The exemplary cascading technique described herein can use, e.g., three assumptions. First, alternating slice-select gradients such as those shown in 80 in FIG. 7a, may cancel previous dephasing to refocus all spins in the volume-of-interest (VOI) at the cascade's end. This condition may be met if the selective gradient areas for all the pulses in the cascade are approximately the same. Second, each pulse can be shortened such that their cumulative length is similar to that of the superposition. Slight TE differences for the various echoes may only cause correctable linear phase shifts and minor $T_2$ loss which can be small and approximately linear in the cascade length as long as it is about 20% or less of $T_2$. Third, because most of the energy of a SINC may be in a central lobe, shortening its duration by truncating side-lobes can have a small effect on the peak $B_1$. If the BW of such lobe is then increased proportionally, the impact on the slice profile of such truncation may be minor as shown, e.g., in FIG. 7a.

FIG. 7a illustrates schematic RF 82 and gradient 84 waveforms for: (a) Two 90° SINCs to HSI-encode two slices with the highest BW (strongest $G_r$) within the $B_1$ limit (dashed line) to minimize values of CSD, shown at 74; (b) Linear superposition of (a), with the "clip" (exceeding the $B_1$ limit), shown at 76; (c) Lowering the pulse BW and $G_r$ proportionally to reduce the peak $B_1$ at a cost to CSD, shown at 78; and (d) HSI pulse synthesized by a cascade of m'=2 single-slice pulses, which can require 1/m' times the $B_1$ value of (b), and which may permit a factor of m' times stronger $G_r$ value than (c), at the expense of some $T_2^*$ loss and (correctable) linear phase shift, shown at 80.

Figure 7B:
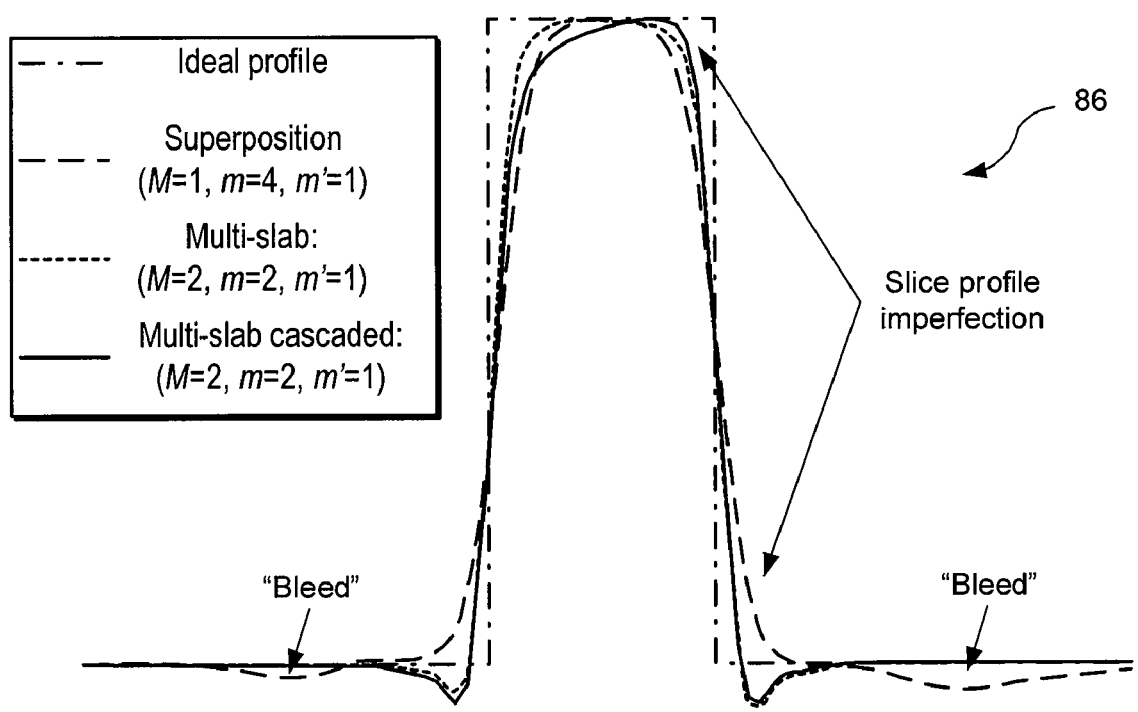
FIG. 7b illustrates slice profiles reconstructed from simulated $4^{th}$ order Hadamard spectroscopic imaging encoding in accordance with the exemplary embodiment of the present invention.

FIG. 7b illustrates exemplary slice profiles 86 reconstructed from simulated, $4^{th}$ order, HSI encoding over a 5 cm VOI using 5.12 ms pulses of $B_1$=0.96 kHz: (i) Superposition under 1.8 mT/m; (ii) multi-slab, M=2, m=2 under 3.6 mT/m; and (iii) multi-slab cascaded under 7.2 mT/m (dashed, dotted and solid lines). The exemplary profile of the superposition (ii) may be preferable to that of (i), and profiles of the multi-slabs (ii) and (iii) appear similar. Due to a $G_r$ value that is twice as strong, (iii) may suffer about half the chemical shift of superposition (ii) and about one-quarter that of (i).

Multi-Slab Cascaded HSI

By combining the two exemplary approaches described above, e.g., segmenting the FOV into M thinner slabs and cascading the m' HSI pulse components instead of superposing them, a greater reduction factor in the peak RF field amplitude can be achieved as suggested by Equations 13 and 14, e.g.:

$$B_1 \propto 1/M \cdot m' \quad [15]$$

Substituting M and m' into Equation 15 suggests that a significant reduction in $B_1$, e.g., down to the value for a single slice, can be achieved with a dramatic decrease in the specific absorption rate ("SAR"). Such decrease can be expressed as, e.g.:

$$SAR \propto (B_1)^2 \propto (1/M \cdot m')^2 \quad [16]$$

If instead of reducing $B_1$, the value of BW is kept high and a slice-select gradient is increased proportionally, the CSD can be lowered by up to a factor of $M \cdot m'$.

Examples of Reducing Chemical Shift Artifacts

To compare slice profile and CSD performance of such superposition, multi-slab and cascaded HSI, exemplary numerical simulations and experiments in a phantom at 3 and 7 T were conducted. These exemplary simulations and experiments included a 5 cm VOI, encoded with about 5.12 ms HSI RF pulses of 0.96 kHz peak $B_1$.

To compare the slice profile obtained by the exemplary embodiments of the present invention (e.g., multi-slab acquisition, pulse cascading in multi-slice HIS, and multi-slab cascaded HSI), numerical solutions of the density matrix equation were obtained based on each technique. The 0.96 kHz peak $B_1$ available at either field mandated a maximum about 1.7 kHz BW to maintain the 5 cm FOV. The slice-select gradients used to accommodate them were 1.8, 3.6 and 7.2 mT/m for multi-slab acquisition, pulse cascading in multi-slice HSI, and multi-slab cascaded HSI, respectively.

All exemplary experiments were performed in a 3 T and 7 T whole-body imager (Siemens AG, Erlangen, Germany) with 25×18 cm diameter depth TEM head coils capable of producing up to 1 kHz $B_1$s at each field. The exemplary phantom (Accurate Lock, Stamford, Conn.) was a 12×5 cm diameter×length plastic cylinder which included four 1.25 cm partitions (including a 1 mm wall) along the short aspect length, immersed in a larger water-filled tube to reduce air-water susceptibility, as shown in FIG. 8, described herein. Each partition contained a different 100 mM in protons solute yielding a singlet at a distinct chemical shift: Methanol (Meth), Na-acetate (NaAc), tert-buthanol (t-BU) and Na-3-Methyl-Silyl propionate (Na-3-Si) at 3.4, 2.2, 1.2 and 0.0 ppm, which may be similar to the ranges typically encountered in vivo.

After auto-shimming, as described in *A Fast, Reliable, Automatic Shimming Procedure Using 1H Chemical-Shift-Imaging Spectroscopy*, Hu et al., J Magn Reson B 1995; 108(3):213-219, incorporated herein by reference in its entirety, the 8×8×5 cm$^3$ VOI was excited with TE/TR=35/1600 ms PRESS. Transverse HSI pulses were used for the 90°. Localization in the anterior-posterior (AP)× left-right (LR) planes of the 16×16 cm$^2$ slices was performed using 16×16 chemical shift imaging (CSI). For all acquisitions, the carrier frequency $\omega_0$ in Equation 9 was at 2.0 ppm. Three HSI schemes and one non-localizing scheme were compared along the 5 cm (IS) aspect of the VOI:

1. Superposition (M=1, m=4, m'=1) of 4$^{th}$ order HSI pulses under a 1.8 mT/m, as shown, e.g., 78 of FIG. 7a.
2. Multi-slab (M=2, m=2, m'=1): two 2$^{nd}$ order superposition-HSI encoded slabs, 2.5 cm each, under 3.6 mT/m, as shown, e.g., in FIG. 6.
3. Multi-slab cascaded (M=2, m=2, m'=2): same as the Multi-slab example above, but with each 2$^{nd}$ order HSI pulse cascaded into two 2.56 ms segments of 1.25 cm, each, under 7.2 mT/m, as shown, e.g., 80 of FIG. 7a.
4. Non-localized (M=1, m=1, m'=1) excitation of an 8$_{IS}$ cm slab. Since the four 1.25 cm bands were in its center, spectra were free of CSD and slice-profile artifacts.

Residual water was removed from the data in the time domain, the signals were apodized with a 1 Hz Lorentzian, and Hadamard and Fourier transformed along the spatial and time directions. Frequency, zero and first (for cascaded pulses only) order phase were automatically corrected in each voxel. Relative levels of the Meth, NaAc, t-BU, or Na-3-Si in each voxel were estimated from their peak areas using the parametric spectral modeling described, e.g., in *Automated Spectral Analysis III: Application to in vivo Proton MR Spectroscopy and Spectroscopic Imaging*, Soher et al., Magn Reson Med 1998; 40(6):822-831, incorporated herein by reference in its entirety.

Exemplary simulated slice profiles for superposition and for multi-slab with and without cascading, are shown in FIG. 7b. To compare performance of these techniques, a rectangle having amplitude "1" at the slice and "0" outside the slice was defined. Pulse-profile imperfections were calculated as ratios of the pulse area within that rectangle to the rectangle's area. Slice "bleed," shown in FIG. 7b, can refer to a ratio of the simulated slice area outside the rectangle to its area inside the rectangle. Imperfections and bleed for each exemplary technique, which are shown in Table 3, suggest that the M=2, m=2 multi-slab (m'=1) and cascaded multi-slab pulse (m'=2) may be similar and can exceed the simple M=1, m=4, m'=1 superposition technique in either metric.

TABLE 3

| Encoding | Selective gradient mT/m | Profile imperfection (%) | "Bleed out" (%) | [1](%) CSD 3 T | | [1](%) CSD 7 T | |
|---|---|---|---|---|---|---|---|
| Superposition M = 1, m = 4, m' = 1 | 1.8 | 9.8 | 14.5 | Meth = <br> [2]NaAc = <br> t-BU = <br> Na-3-Si = | 14% <br> 10% <br> 11% <br> 32% | Meth = <br> [2]NaAc = <br> t-BU = <br> Na-3-Si = | 44% <br> 14% <br> 20% <br> 75% |
| Multi-slab M = 2, m = 2, m' = 1 | 3.6 | 4.5 | 5.1 | [2]Meth = <br> [2]NaAc = <br> [2]t-BU = <br> Na-3-Si = | 5% <br> 5% <br> 6% <br> 15% | Meth = <br> [2]NaAc = <br> [2]t-BU = <br> Na-3-Si = | 17% <br> 5% <br> 9% <br> 40% |
| Multi-slab cascaded | 7.2 | 5.8 | 4.9 | [2]Meth = <br> [2]NaAc = | 3% <br> 5% | Meth = <br> [2]NaAc = | 13% <br> 3% |

TABLE 3-continued

| Encoding | Selective gradient mT/m | Profile imperfection (%) | "Bleed out" (%) | [1](%) CSD 3 T | | [1](%) CSD 7 T | |
|---|---|---|---|---|---|---|---|
| M = 2, m = 2, m' = 2 | | | | [2]t-BU = [2]Na-3-Si = | 3% 2% | [2]t-BU = [2]Na-3-Si = | 4% 5% |

[1]Calculated based on Equation 17.
[2]Leakage dominated by slice imperfections; see, e.g., FIGs. 7a and 7b.

Table 3 shows the experimental exemplary parameters and slice profile performance of the three HSI techniques described herein with respect to exemplary embodiments of the present invention. Each technique was applied using the same 5.0 cm VOI, 0.96 kHz peak $B_1$ and 5.12 ms pulse length. A similarity in slice profile imperfection (numerical simulation) is shown between the multi-slab and cascaded multi-slab, as well as reduced "bleed out" of the latter due to the stronger $G_r$. A reduction in CSD was observed from the superposition to multi-slab to cascaded multi-slab exemplary technique at each value of $B_0$, especially for Na-3-Si, as shown in FIG. 9, described below.

Experiments performed using the whole-body imagers as described above were run consecutively on the phantom to ensure common acquisition parameters at each field. Spectra from a column of four voxels along the HSI (IS) direction observed for each exemplary experiment and $B_0$ value are shown in FIGS. 8a-8c. FIG. 8a illustrates an exemplary sagittal image 90 of the phantom showing the partitions containing Methanol (Meth), Na-acetate (NaAc), tert-buthanol (t-BU), and Na-3-Methyl-Silyl propionate (Na-3-Si). FIG. 8b illustrates an absolute 3 T spectrum 92 from a $1_{AP} \times 1_{LR} \times 8_{IS}$ cm³ voxel showing 100 mM proton concentrations singlets at 3.4, 2.2, 1.2 and 0.0 ppm. FIG. 8c illustrates exemplary spectra from 4 voxel columns along the IS direction encoded with superposition, multi-slab, and cascaded multi-slab HSI under 1.8, 3.6 and 7.2 mT/m on common frequency and intensity scale at each value of $B_0$. The voxel columns are shown at 94 for Na-3-Si, 96 for t-BU, 98 for NaAc, and 100 for Meth. Parameters used in these analyses include a peak value of $B_1 = 0.96$ kHz, a 5.12 ms pulse duration, TE=35 ms, and TR=1.6 s. Slice-profile errors are indicated by dashed ellipses and CSD values are marked with arrows, and are estimated in Table 3. The following errors appear to increase as shown: (i) at 7 vs. 3 T; (ii) for the weaker $G_r$ (superposition) versus the strongest (cascade) technique; for example (iii) metabolites with greater $\Delta\omega$, e.g., greater value of CSD (Meth, t-BU, Na-3-Si).

The CSD appear as interslice "leakage" which may be greater at 7 T than at 3 T. Slice-profile errors are approximately unchanged, because the same sequence was used at both fields, discussed in *Reducing Voxel Bleed in Hadamard-Encoded MRI and MRS*, Goelman et al., Magn Reson Med 2006; 55(6):146-1465.

FIG. 9 is a schematic illustration 102 of an exemplary location of the four HSI RF excitation bands for all "on carrier" at 2.0 ppm resonances (solid lines). The dashed lines indicate where the slices are actually sampled, e.g., the effective location of their metabolites (analogous to FIG. 8c) due to their different CSD values (dashed lines). The thin arrows show the relative magnitude and direction of the CSD, $\Delta r$ of Equation 11 from the centers of the RF slices. As shown, the NaAC, commonly "on carrier," may pick up contamination from both neighbors (see also FIGS. 8a-8c).

To estimate displacement error, the ratio of the signal expected in a slice to the sum of that metabolite from adjacent slices was calculated, e.g.:

$$\% \text{ Leakage} \approx \left[ 1 - \frac{\text{signal in slice}}{\text{signal in slice} + \text{signal in adjacent slices}} \right] \cdot 100 \quad [17]$$

These exemplary percentages can be shown in Table 3. Approximately 5-15% of the "contamination" in each voxel can be ascribed to various RF pulse imperfections such as those shown in FIGS. 7a, 7b, and 8a-8c and quantified in Table 3. The remainder may be associated with CSD, as shown in FIG. 9. For example, with the NaAc at $\Delta\omega_i = 0.2$ ppm (from carrier, $\omega_0$, at 2 ppm), $\Delta r$ of Equation 11 is smaller than the value for the more distal peaks, e.g., t-BU, Na-3-Si and Meth at $\Delta\omega_i = 0.7$, 1.4 and 2.0 ppm, at either field value. Such values of $\Delta r$ may be about half as large at 3 T than at 7 T, as shown in Table 3 and in FIGS. 8a-8c.

For example, less desirable results may correspond to the superposition pulse on Na-3-Si, with $\Delta\omega$ of 2.0 ppm=250 from a carrier at 3 T and 600 Hz at 7 T. The value of $G_r$ used, 756 Hz/cm (using a 1.8 mT/m gradient), rendered $\Delta r = 0.4$ cm at 3 T and 0.8 cm at 7 T. For a 1.25 cm slice, such shifts represent about 30% or 64% at 3 T or 7 T CSD, respectively, as shown in FIG. 9. This can lead to a significant signal loss, as shown in the top row of FIG. 8c. Further, the "superposition" pulse corresponding to the NaAc slice (having a weak 1.8 mT/m gradient) exhibited contamination from both sides (Meth and t-BU) at either field, as shown, e.g., in FIGS. 8a-8c. With $\Delta\omega = 0.2$ ppm and $\Delta r \approx 0$, exemplary contaminations can correspond to CSD from neighbors on either side, as illustrated in FIG. 9.

Metabolite signals obtained using the multi-slab acquisition technique may be compared to those obtained using the multi-slab technique with cascading at either fields. As shown in FIGS. 8a-8c, such comparison suggests that losses from progressive $T_2^*$ decay or incomplete signal rephasing may be negligible, at least in a well-shimmed phantom.

Optimal SNR and efficiency (in terms of duty cycle) in 3D MRSI may favor a multi-slab approach. In the human brain, practical consideration of VOI size, spatial resolution, SNR and total measurement time, may dictate few slices per slab, e.g., m=2 to 4. Such few partitions can favor RF encoding (e.g., as compared with gradient encoding) due to a preferable point-spread-function. The sensitivity at 7 T may be sufficient for (0.5 cm)³ voxels. Accordingly, the CSD that selective pulses incur can represent about 200% relative localization error, or a "mere" ~100% at 3 T, which indicates both the problem and the importance of strong gradients.

This artifact can be apparent in the exemplary phantom as shown, e.g., in FIGS. 8a-8c. Because each partition may contain only one distinct singlet, any other peaks in that slice may generally arise from localization errors, e.g., either profile imperfection or CSDs. In contrast, in the brain or any other homogeneous or quasi-homogeneous medium, any voxel may contain some or all metabolites. In such systems, since no prior knowledge is available on how much of the signal in any given voxel is intrinsic (e.g., versus leakage in or out), both spatial and spectral quantification may be subject to uncertainty.

While a simple exemplary remedy for such uncertainty may be to increase a selection gradient, a practical peak $B_1$ and SAR limitation, particularly at high values of $B_0$, may preclude such "brute-force" approach. In accordance with exemplary embodiments of the present invention, the multi-slab and cascading techniques described herein can each or together reduce such displacement into insignificance, as shown, e.g., in Table 3 and in FIGS. 8a-8c. Further, SNR and efficiency edges may be retained. Both exemplary techniques also can utilize the property that Hadamard slices do not have to be contiguous to interleave them, as shown in FIG. 6, and may thereby reduce the amount of "bleed" from slice-imperfection to under about 5%, as shown in Table 3 and in FIGS. 8a-8c. Stronger gradients which may be afforded by these exemplary techniques, therefore, can improve localization via two mechanisms: better slice-profile and less displacement.

The multi-slab exemplary technique, with or without cascading, may be applied in only one direction. The other two directions, therefore, can be gradient phase encoded ("CSI"). Cascading alone, however, may be applied in any RF-encoded direction(s), e.g., for multi-dimensional HIS, as discussed in *Hadamard Spectroscopic Imaging Techniques as Applied to Study Human Calf Muscles*, Goelman et al., Magn Reson Med 1992; 25:349-354, the entire disclosure of which is incorporated herein by reference. While CSI may not suffer from CSD per se, the selective pulses used to define the VOI may do so, which can affect voxels at edges of the VOI that therefore may be frequently discarded. This effect can persist even for rigorous outer volume suppression which can prevent "leakage-in" losses but not "leakage-out" losses.

Cascading can also encounter progressive $T_2^*$ decay for earlier pulses in a chain. With voxel $T_2^*$ values of ~70 and ~35 ms at 3 and 7 T, respectively, a 2.5 ms delay can represents about 3-7% signal loss, which may be similar to voxel noise-to-signal fractions common in 3D in vivo $^1$H-MRSI. Linear phase shifts from progressive delays in the cascade may be corrected in post-processing, as shown in FIGS. 8a-8c. Further, while slice profiles of shorter cascaded pulses may be nearly identical to longer superpositions due to higher BW, as shown, e.g., in FIGS. 7a and 7b, such advantage may not be limitless. For example, as m' increases to 4 or 8 pulses, the single-slice building blocks may shorten to avoid $T_2^*$ loss. Because slice thickness and peak $B_1$ value can preclude further BW increases, improvements in cascade length may lead to an impairment of slice profile.

Higher RF power which may be utilized to generate the same $B_1$ amplitude at higher values of $B_0$ may raise other concerns, such as SAR safety. For example, the 2 to 5 kW RF power levels and inhomogeneous distribution of their energy deposition, "hot spots" can place a severe-to-prohibitive limitation on pulse lengths, number, peak $B_1$ value, and/or the TR. Since a linear reduction in $B_1$ can lead to a quadratic decrease in SAR, the exemplary techniques described herein can be used to mitigate safety restrictions in order to extract the maximal sensitivity and efficiency advantages from high and ultra-high field imagers.

Exemplary multi-slab techniques, with or without cascading, can dramatically reduce the peak values of $B_1$ which may be needed for RF phase encoding schemes that may be optimal in both SNR and efficiency. Such reduction of $B_1$ can be used, for, e.g.: (i) increasing a selection gradient to reduce the CSD to an insignificant level and improve the slice profile, even at 7 T; or (ii) lowering $B_1$ for a quadratic decrease in SAR, which may address a critical safety concern and limitation at the higher values of $B_0$ that are approved for human use, e.g., up to 8 T. Since either technique can be relatively simple to implement, both may be readily applicable to any modern MR imager.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced herein are incorporated herein by reference in their entireties.

What is claimed is:

1. A method for generating data associated with at least one portion of a target comprising:
    forwarding at least one excitation pulse to the target;
    acquiring a signal from the target resulting from the at least one excitation pulse, wherein the signal from the target is acquired by (i) segmenting a field of view of the at least one portion of the target into a predetermined number of slabs that are acquired sequentially during each repetition time, and wherein each of the slabs comprises a plurality of slices, and (ii) multiplexing the slabs in time and the slices in space; and
    using a hardware processing arrangement, generating the data based on the acquired signal.

2. The method of claim 1, wherein the predetermined number (M) is determined as follows: $M=TR_{opt}/T_c$, wherein $TR_{opt}$ is an optimal repetition time and $T_c$ is an acquisition cycle.

3. The method of claim 1, wherein multiplexing in space comprises an acquisition of multiple voxels.

4. The method of claim 3, wherein repetition time (TR) extends beyond an acquisition cycle of the signal.

5. The method of claim 1, wherein the target is an anatomical structure.

6. The method of claim 1, wherein the data is a magnetic resonance readout.

7. The method of claim 1, wherein the data is image data, and wherein the image data is generated based on the acquired signal.

8. The method of claim 1, wherein the excitation pulse is forwarded according to a magnetic resonance spectroscopy imaging pulse sequence.

9. The method of claim 1, wherein the excitation pulse comprises a series of Hadamard pulse components and wherein the pulses components are cascaded.

10. The method of claim 1, further comprising: at least one of displaying or storing the data in a storage arrangement in at least one of a user-accessible format or a user-readable format.

11. The method of claim 1, wherein the plurality of slices are multiplexed in space and the predetermined number of slabs are multiplexed in time so that at least one of (i) the slices associated with each slab is proportional to a total number of the slices associated with the at least one portion of the target, or (ii) a total number of the slabs associated with the at least one portion of the target is independent of the total number of the slices associated with the at least one portion of the target.

12. A non-transitory computer accessible medium having stored thereon computer executable instructions for generating data associated with at least a portion of a target which, when the executable instruction are executed by a processing arrangement, configure the processing arrangement to perform a procedure comprising:
forwarding at least one excitation pulse to the target;
acquiring a signal from the target resulting from the at least one excitation pulse, wherein acquiring the signal from the target is performed by (i) segmenting a field of view of the at least one portion of the target into a predetermined number of slabs that are acquired sequentially during each repetition time, and wherein each of the slabs comprises a plurality of slices, and (ii) multiplexing the slabs in time and the slices in space; and
generating the data based on the acquired signal.

13. The computer accessible medium of claim 11, wherein the predetermined number (M) is determined as follows: $M = TR_{opt}/T_c$, wherein $TR_{opt}$ is an optimal repetition time and $T_c$ is an acquisition cycle.

14. The computer accessible medium of claim 12, wherein multiplexing in space comprises an acquisition of multiple voxels.

15. The computer accessible medium of claim 14, wherein repetition time (TR) extends beyond an acquisition cycle of the signal.

16. The computer accessible medium of claim 12, wherein the target is an anatomical structure.

17. The computer accessible medium of claim 12, wherein the data is a magnetic resonance readout.

18. The computer accessible medium of claim 12, wherein the data is image data, and wherein the image data is generated based on the acquired signal.

19. The computer accessible medium of claim 12, wherein the excitation pulse is forwarded according to a magnetic resonance spectroscopy imaging pulse sequence.

20. The computer accessible medium of claim 12, wherein the plurality of slices are multiplexed in space and the predetermined number of slabs are multiplexed in time so that at least one of (i) the slices associated with each slab is proportional to a total number of the slices associated with the at least one portion of the target, or (ii) a total number of the slabs associated with the at least one portion of the target is independent of the total number of the slices associated with the at least one portion of the target.

21. A method for generating data associated with at least one portion of a target, comprising:
providing at least one excitation pulse to the target, wherein the at least one excitation pulse comprises a series of Hadamard pulse components, and wherein the pulses components are cascaded;
acquiring a signal from the target resulting from the at least one excitation pulse; and
using a hardware processing arrangement, generating the data based on the acquired signal.

22. The method of claim 21, wherein the signal from the target is acquired by (i) segmenting a field of view of the at least one portion of the target into a predetermined number of slabs that are acquired sequentially during each repetition time, and wherein each of the slabs comprises a plurality of slices, and (ii) multiplexing the slabs in time and the slices in space.

23. The method of claim 22, wherein multiplexing in space comprises an acquisition of multiple voxels.

24. The method of claim 22, wherein the target is an anatomical structure.

25. The method of claim 22, wherein the data is a magnetic resonance readout.

26. The method of claim 22, wherein the data is image data, and wherein the image data is generated based on the acquired signal.

27. The method of claim 22, wherein the excitation pulse is forwarded according to a magnetic resonance spectroscopy imaging pulse sequence.

28. The method of claim 21, wherein the plurality of slices are multiplexed in space and the predetermined number of slabs are multiplexed in time so that at least one of (i) the slices associated with each slab is proportional to a total number of the slices associated with the at least one portion of the target, or (ii) a total number of the slabs associated with the at least one portion of the target is independent of the total number of the slices associated with the at least one portion of the target.

29. The method of claim 21, further comprising: at least one of displaying or storing the data in a storage arrangement in at least one of a user-accessible format or a user-readable format.

30. A non-transitory computer accessible medium having stored thereon computer executable instructions for generating data associated with at least a portion of a target which, when the executable instruction are executed by a processing arrangement, configure the processing arrangement to perform a procedure, comprising:
providing at least one excitation pulse to the target, wherein the at least one excitation pulse comprises a series of Hadamard pulse components, and wherein the pulses components are cascaded;
acquiring a signal from the target resulting from the at least one excitation pulse; and
generating the data based on the acquired signal.

31. The computer accessible medium of claim 30, wherein the signal from the target is acquired by (i) segmenting a field of view of the at least one portion of the target into a predetermined number of slabs that are acquired sequentially during each repetition time, and wherein each of the slabs comprises a plurality of slices, and (ii) multiplexing the slabs in time and the slices in space.

32. The computer accessible medium of claim 31, wherein multiplexing in space comprises an acquisition of multiple voxels.

33. The computer accessible medium of claim 29, wherein the plurality of slices are multiplexed in space and the predetermined number of slabs are multiplexed in time so that at least one of (i) the slices associated with each slab is proportional to a total number of the slices associated with the at least one portion of the target, or (ii) a total number of the slabs associated with the at least one portion of the target is independent of the total number of the slices associated with the at least one portion of the target.

34. The computer accessible medium of claim 30, wherein the target is an anatomical structure.

35. The computer accessible medium of claim 30, wherein the data is a magnetic resonance readout.

36. The computer accessible medium of claim 30, wherein the data is image data, and wherein the image data is generated based on the acquired signal.

37. The computer accessible medium of claim 30, wherein the excitation pulse is forwarded according to a magnetic resonance spectroscopy imaging pulse sequence.

* * * * *